United States Patent [19]

Jeganathan et al.

[11] Patent Number: 5,780,625
[45] Date of Patent: Jul. 14, 1998

[54] 4-AMINOPHENOL DERIVATIVES

[75] Inventors: Suruliappa Gowper Jeganathan; Christophe Bulliard, both of Fribourg, Switzerland

[73] Assignee: Ciba Specialty Chemicals Corporation, Tarrytown, N.Y.

[21] Appl. No.: 756,222

[22] Filed: Nov. 25, 1996

[30] Foreign Application Priority Data

Nov. 27, 1995 [CH] Switzerland ............... 3361/95
Jan. 8, 1996 [CH] Switzerland ............... 48/96

[51] Int. Cl.⁶ ............... C07D 265/30; C07D 279/12
[52] U.S. Cl. ............... 544/58.2; 544/58.1; 544/59; 544/60; 544/171; 544/174
[58] Field of Search ............... 544/58.1, 59, 60, 544/171, 174, 58.2

[56] References Cited

U.S. PATENT DOCUMENTS

| | | | |
|---|---|---|---|
| 3,935,016 | 1/1976 | Nishimura et al. | 96/74 |
| 4,452,884 | 6/1984 | Leppard | 430/551 |
| 4,465,765 | 8/1984 | Leppard et al. | 430/512 |

FOREIGN PATENT DOCUMENTS

| | | |
|---|---|---|
| 0082817 | 12/1982 | European Pat. Off. |
| 0103540 | 8/1983 | European Pat. Off. |
| 0113124 | 12/1983 | European Pat. Off. |
| 0273712 | 12/1987 | European Pat. Off. |
| 0457543 | 5/1991 | European Pat. Off. |
| 9522082 | 2/1995 | WIPO |

*Primary Examiner*—Richard L. Raymond
*Attorney, Agent, or Firm*—Luther A. R. Hall

[57] ABSTRACT

A description is given of novel O-phenol-substituted aminophenol derivatives of the formula

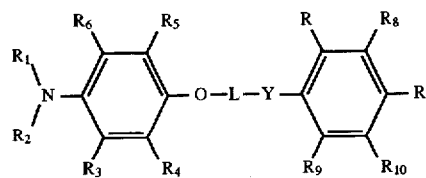

in which the symbols are as defined in claim 1, which can be used in particular as stabilizers for magenta couplers in color-photographic recording materials.

22 Claims, No Drawings

4-AMINOPHENOL DERIVATIVES

The present invention relates to novel 4-aminophenol derivatives, to processes for their preparation and to the use thereof, especially in colour-photographic recording materials, to novel colour-photographic recording materials and to processes for stabilizing magenta couplers and magenta dyes in colour-photographic recording materials, and to novel intermediates.

The presence of a stabilizer in magenta couplers in colour-photographic recording materials is known. Alkylated hydroquinone ethers or diethers used to date as stabilizers in colour-photographic recording materials have shown inadequate activity, especially with 1H-pyrazolo[5,1-c][1,2,4]triazole magenta couplers. Furthermore, EP-A-273 712, for example, describes a magenta coupler with a stabilizer which includes ring nitrogen, and EP-A-457 543 describes a magenta coupler with a dual combination of stabilizer. Furthermore, phenolic compounds have already been proposed as stabilizers for colour-photo-graphic recording materials, for instance in EP-A-82 817, EP-A-103 540, U.S. Pat. No. 3,935,016 or EP-A-113 124. Although such stabilizers have led to an increase in the photostability of colour photographs, they have not achieved the desired enhancement of stabilization. In this context mention may also be made of WO-A-95 22082, which describes specifically substituted aminophenol derivatives which can be used as stabilizers for magenta couplers in colour-photographic recording materials.

One of the objects of the invention was, in general, to develop compounds which comprehensively improve the image quality.

Novel O-phenol-substituted aminophenol derivatives have now been found which are, surprisingly, suitable for use as stabilizers for colour couplers, especially for magenta couplers in colour-photographic recording materials. They are additionally suitable as coupler oil and therefore make it possible to incorporate the couplers more easily. In particular, this group of novel O-phenol-substituted aminophenol derivatives is suitable for increasing the stability of magenta couplers and magenta dyes in colour-photographic materials.

The novel O-phenol-substituted aminophenol derivatives are compounds of the general formula I

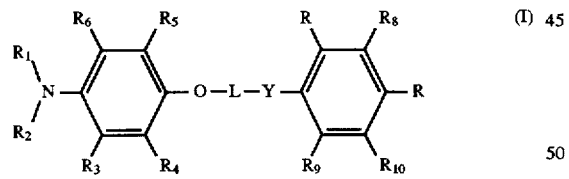

in which one R is the group —OH and the other R is the group $R_7$, and in which:

L is a direct bond or a bridging link of the formulae:
—CO—($C_1$–$C_{18}$alkylene)$_m$—,
—$C_1$–$C_{18}$alkylene-Q–$C_1$–$C_{18}$alkylene—,
—$C_1$–$C_{18}$alkylene-Q—$C_1$–$C_{18}$alkylene—O—,
—$C_1$–$C_{18}$alkylene-Q—$C_1$–$C_{18}$alkylene-O—CO—($C_1$–$C_{18}$alkylene)$_m$—,
—$C_1$–$C_{18}$alkylene-CH($R_0$)—O—CO—($C_1$–$C_{18}$alkylene)$_m$—,
—$C_1$–$C_{18}$alkylene-Q—$C_1$–$C_{18}$alkylene-CO—O—$C_1$–$C_{18}$alkylene,
—$C_1$–$C_{18}$alkylene-Q—$C_1$–$C_{18}$alkylene-CO—O—$C_1$–$C_{18}$alkylene-O—CO—,
—$C_1$–$C_{18}$alkylene-Q—$C_1$–$C_{18}$alkylene-CO—O—$C_1$–$C_{18}$alkylene-N($R_{11}$)—CO—,
$C_2$–$C_{24}$alkylene,
$C_2$–$C_{24}$alkylene containing one or more heteroatoms in the chain,
$C_2$–$C_{18}$alkenylene,
$C_3$–$C_{24}$alkenylene containing one or more O atoms in the chain, or a bridging link of the formula

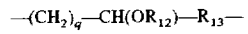

in which:

Q is a direct bond or is —O—, —S—, —SO—, —SO$_2$—, —N($R_{11}$)—, —CH($R_0$)—, —CO—N($R_{11}$), —N($R_{11}$)—CO— or —O—CO—N($R_{11}$)—, m is zero or 1, and q is an integer from 1 to 18;

Y is a direct bond or a divalent bridging link of the formula

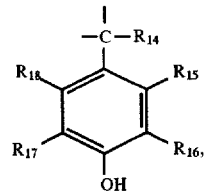

$R_0$ is $C_1$–$C_{18}$alkyl or is $C_2$–$C_{24}$alkyl containing one or more O atoms in the chain, or is a group of the formula

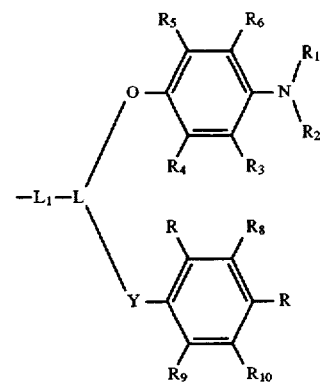

in which $L_1$ is $C_2$–$C_{18}$alkylene or

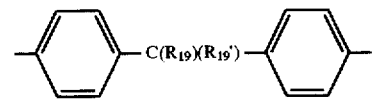

and is connected to the remainder of the molecule by way of a radical L which includes Q(CHR$_0$) or CHR$_0$. $R_1$ and $R_2$, independently of one another, are H, $C_1$–$C_{18}$alkyl, $C_3$–$C_{24}$alkyl interrupted by 1 or more O atoms, $C_1$–$C_{18}$alkenyl, $C_5$–$C_8$cycloalkyl, unsubstituted or substituted aryl, radicals of the formula

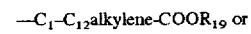

in which $R_{30}$ is $C_1$–$C_{18}$alkyl, and where $R_1$ and $R_2$ together may also form a ring including the divalent group of the formula

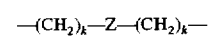

in which each index k. independently of the other. is an integer from 1 to 3. and Z is the group —O—. —S—. —SO—. —SO$_2$—. —N(R$_{11}$)—. —CH$_2$—. —O—SO—O—. —O—B(R$_{20}$)—O—. —O—P(R$_{21}$)—O— or 13 N(R$_{11}$)—(CH$_2$)$_g$—N(R$_{11}$)—, where g is an integer from 1 to 3;

R$_3$ to R$_{10}$ independently of one another are H. C$_1$–C$_{18}$alkyl. C$_2$–C$_{18}$alkenyl. C$_1$–C$_{12}$alkoxy. C$_5$–C$_8$cycloalkyl, unsubstituted or substituted aryl, or halogen, where R$_8$ and R$_{10}$ independently of one another may also be a group of the formula

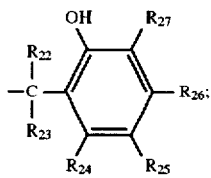

R$_1$ and R$_{11}$' independently of one another are H. C$_1$–C$_{18}$alkyl. C$_2$–C$_{18}$alkenyl, unsubstituted or substituted aryl or a group —COR$_{28}$;

R$_{12}$ is H, C$_1$–C$_{18}$alkyl. C$_2$–C$_{18}$alkenyl or a group of the formula —COR$_{28}$;

R$_{13}$ is a divalent bridging link of the formula —(O)$_m$—C$_1$–C$_{18}$alkylene—(O)$_m$—. —O—C$_1$–C$_{18}$alkylene-O—CO—, or —O—C$_1$–C$_{18}$alkylene-O—CO—(C$_1$–C$_{18}$alkylene)$_m$—;

R$_{14}$ is H, C$_1$–C$_{18}$alkyl. C$_2$–C$_{18}$alkenyl. C$_3$–C$_8$cycloalkyl, C$_3$–C$_{24}$alkyl interrupted by one or more O atoms. unsubstituted or substituted aryl, an unsubstituted or substituted heterocycle, or a group of the formula —C$_1$–C$_{12}$alkylene-COO-R$_{29}$ or —C$_1$–C$_{12}$alkylene-CO—NR$_{11}$R$_{11}$';

R$_{15}$ to R$_{18}$ independently of one another are H. C$_1$–C$_{18}$alkyl. C$_2$–C$_{18}$alkenyl. C$_1$–C$_{12}$alkoxy C$_5$–C$_8$cycloalkyl, unsubstituted or substituted aryl, or halogen;

R$_{19}$ and R$_{19}$' independently of one another are H. C$_1$–C$_{18}$alkyl. C$_2$–C$_{18}$alkenyl or unsubstituted or substituted aryl;

R$_{20}$ and R$_2$. are C$_1$–C$_8$alkyl or unsubstituted or substituted aryl;

R$_{22}$ and R$_{23}$ independently of one another are H. C$_1$–C$_{18}$alkyl. C$_3$–C$_{24}$alkyl interrupted by one or more O atoms; C$_2$–C$_{18}$alkenyl; C$_5$–C$_8$cycloalkyl; unsubstituted or substituted aryl or a group of the formula —C$_1$–C$_{12}$alkylene-COOR$_{18}$;

R$_{24}$ to R$_{27}$ independently of one another are H. C$_1$–C$_{18}$alkyl, C$_2$–C$_{18}$alkenyl. C$_1$–C$_{12}$alkoxy. C$_5$–C$_8$cycloalkyl, unsubstituted or substituted aryl, halogen or a group of the formula —C$_1$–C$_{12}$alkylene-COOR$_{29}$;

R$_{28}$ and R$_{29}$ independently of one another are C$_1$–C$_{18}$alkyl. C$_2$–C$_{18}$alkenyl. C$_5$–C$_8$cycloalky or unsubstituted or substituted aryl, and R$_{29}$ is otherwise a group of the formula

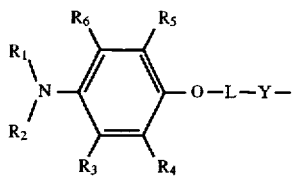

provided that R$_{25}$ is a group of the formula

—C$_1$–C$_{12}$alkylene-COOR$_{29}$ in which Y is a direct bond, and the other symbols R$_1$. R$_2$, R$_3$, R$_4$, R$_5$, R$_6$ and L are as defined, with the exception of compounds of the formula

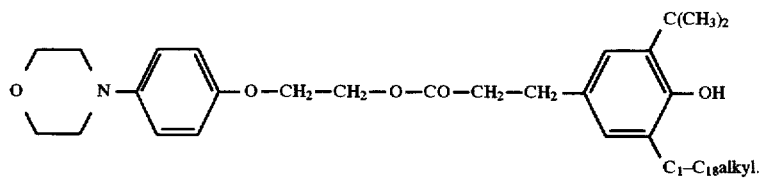

Examples of R$_0$, R$_1$ to R$_{12}$ and R$_{14}$ to R$_{30}$ as C$_1$–C$_{18}$alkyl, which may be branched or unbranched, are radicals such as methyl, ethyl, propyl, butyl, pentyl, hexyl, heptyl, octyl, nonyl, decyl, undecyl, dodecyl, tetradecyl, hexadecyl and octadecyl and also corresponding branched isomers, such as isopropyl, sec-butyl, isobutyl, tert-butyl, 2-ethylbutyl, isopentyl, 1-methylpentyl, 1,3-dimethylbutyl, 1-methylhexyl, isoheptyl, 1,1,3,3-tetramethylbutyl, 1-methylheptyl, 3-methylheptyl, 2-ethylhexyl, 1,1,3-trimethylhexyl, 1,1,3,3-tetramethylpentyl, 1-methylundecyl and 1,1,3,3,5,5-hexamethylhexyl. These radicals may also be substituted one or more times, for example by OH, or halogen (Cl, Br, F, I). Preference is given to C$_1$–C$_{12}$alkyl radicals, especially C$_1$–C$_6$alkyl radicals. Corresponding alkylene radicals as occur in various substituents may likewise be straight-chain or branched and are derived, for example, from the alkyl radicals listed above. Preferred chain lengths apply analogously. Examples of R$_0$, R$_1$, R$_2$, R$_{14}$, R$_{22}$ and R$_{23}$ as a C$_2$ or C$_3$–C$_{24}$alkyl radical interrupted by one or more O atoms are groups of the formulae —(CH$_2$CH$_2$O)$_{1-11}$—CH$_3$, —(CH$_2$CH$_2$O)$_{1-11}$—C$_2$H$_5$, especially CH$_3$—O—CH$_2$CH$_2$—O—CH$_2$—, CH$_3$—(O—CH$_2$—CH$_2$—)$_2$—O —CH $_2$—(O—CH$_2$—CH$_2$—)$_3$—O—CH$_2$— and CH$_3$—(O—CH$_2$—CH$_2$—)$_4$—O—CH$_2$—.

Examples of R$_1$ to R$_{12}$, R$_{14}$ to R$_{19}$ and R$_{22}$ to R$_{29}$ as a C$_2$–C$_{18}$alkenyl radical are branched or unbranched radicals which may be monounsaturated or, from 4 carbon atoms upward, may be polyunsaturated; named examples are 1-propenyl, allyl, methallyl, 2-butenyl, 3-butenyl, isobutenyl, 2-pentenyl, n-2,4-pentadienyl, 3-methyl-2-butenyl, 2-hexenyl, n-2-octenyl, 4-tert-butyl-2-butenyl, n-2-dodecenyl, isododecenyl, oleyl, n-2-octadecenyl and n-4-octadecenyl.

Examples of $R_1$ to $R_{10}$, $R_{14}$ to $R_{18}$ and $R_{22}$ to $R_{29}$ as a $C_5$–$C_8$cycloalkyl radical are cyclopentyl, cyclohexyl, cycloheptyl or cyclooctyl unsubstituted or substituted by 1 to 4 methyl groups, examples being methylcyclopentyl, dimethylcyclopentyl, methylcyclohexyl, 1,3-dimethylcyclohexyl, trimethylcyclohexyl or 1-methyl-4-isopropylcyclohexyl.

Examples of $R_1$ to $R_{11}$ and $R_{14}$ to $R_{29}$ as an unsubstituted or substituted aryl radical are a phenyl or naphthyl radical, especially an (x-naphthyl radical, which can be substituted, in which case examples of suitable substituents are halogen, —COOH, —OH, —SH, especially $C_1$–$C_{12}$alkyl and $C_1$–$C_{12}$alkoxy ( such as methoxy, ethoxy, propoxy, butoxy, isobutoxy), and then —NO$_2$, —NH$_2$, —NH—CO—NH$_2$, —NH($C_1$–$C_4$alkyl), —N($C_1$–$C_4$alkyl)$_2$ and —S($C_1$–$C_4$alkyl). Examples which may be mentioned in this context are o-, m- and p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl, 2,6-diethylphenyl, 2-methylnaphthyl, 1-methylnaphthyl, 4-methylnaphthyl, 2-ethylnaphthyl and 2,6-diethylnaphthyl. Preferred examples of $R_3$ to $R_{10}$, $R_{15}$ to $R_{18}$ and $R_{24}$ to $R_{27}$ as a $C_1$–$C_{12}$alkoxy radical are methoxy, ethoxy, propoxy, butoxy, hexyloxy, heptyloxy, octyloxy and decyloxy and also corresponding branched isomers, such as isopropoxy, isobutoxy and isopentyloxy.

Examples of $R_3$ to $R_{10}$, $R_{15}$ to $R_{18}$ and $R_{24}$ to $R_{27}$ as halogen are fluorine, chlorine, iodine and bromine.

An example of $R_{14}$ as an unsubstituted or substituted heterocycle is a five-membered heterocycle having an atom which is other than carbon, such as —S—, —O— and —NH—; examples are furan, thiophene, pyrrole, pyrrolidone, pyroglutamic acid, maleimides, hydantoin, uracils of the formula

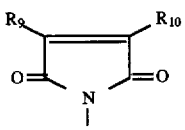

(in which $R_9$ and $R_{10}$ independently of one another are hydrogen, $C_1$–$C_4$alkyl, especially methyl, and halogen such as F, Cl, Br; $R_9$ and $R_{10}$ are preferably hydrogen and methyl), or $R_{14}$ comprises five-membered heterocycles having two atoms other than carbon, such as —O—, —S— or —NH—, examples being oxazole, isoxazole, thiazole, imidazole, hydantoins of the formula

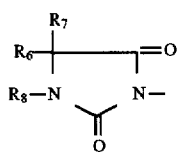

(in which $R_6$, $R_7$ and $R_8$ independently of one another are hydrogen or an unsubstituted $C_1$–$C_6$alkyl group or a $C_1$–$C_6$alkyl which is substituted one or more times by, for example, COOH or COO($C_1$–$C_4$alkyl)) and pyrazole; or comprises five-membered heterocycles having three or more atoms other than carbon, such as —O— and —NH—, examples being furazane, 1,2,3-triazole, 1,2,4-triazole, 1,3,4-triazole and tetrazole; or comprises six-membered heterocycles having one atom other than carbon, for example —O—, —S— or —NH—, examples being pyran, thiopyran, pyridine and quinoline; or comprises six-membered heterocycles having more than one atom other than carbon, such as —N—, examples being diazines such as oiazine, miazine, a dihydrouracil of the formula

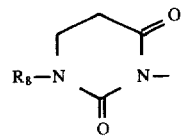

(in which $R_8$ is as defined above) and piazine, vicinal, asymmetric or symmetric triazine, and 1,2,3,4-triazine, 1,2,3,5-triazine and 1,2,4,5-triazine.

Where these heterocyclic groups are substituted, examples of suitable substituents are halogen, —COOH, —OH, —SH, especially $C_1$–$C_{12}$alkyl and $C_1$–$C_{12}$alkoxy (such as methoxy, ethoxy, propoxy, butoxy, isobutoxy), and then —NO$_2$, —NH$_2$, —NH($C_1$–$C_4$alkyl), —NH, CO, —N($C_1$–$C_4$alkyl)$_2$, and also phenyl (unsubstituted or substituted by, for example, —OH, -halogen, —S($C_1$–$C_4$alkyl)).

Preferred heterocycles are five-membered heterocycles having one atom other than carbon, such as thiophene and furan which is unsubstituted or is substituted by alkyl, alkoxy or halogen.

L as $C_2$–$C_{24}$alkylene containing one or more heteroatoms is, for example: a straight-chain or branched-chain bridging link such as ethylene, propylene, n-1-butylene, 2-butylene, n-amylene, 1-hexylene, 1-heptylene, 1-octylene, 1-nonylene, 4-ethyl-2-hexylene, 2-methylenepentane and 4-ethen-4-ylheptane, which can be interrupted one or more times by heteroatoms such as —O—, —S—, —SO—, —SO$_2$—, —N($R_1$)—.

Examples are: —CH$_2$—O—CH$_2$—, —CH$_2$—S—CH$_2$—, —CH$_2$—NH—CH$_2$—, —CH$_2$—N(CH$_3$)—CH$_2$—, —CH$_2$—O—CH$_2$CH$_2$—O—CH$_2$—, —CH$_2$—(O—CH$_2$CH$_2$—)$_2$—O—CH$_2$—, —CH$_2$—(O—CH$_2$CH$_2$—)$_3$—O—CH$_2$— or —CH$_2$—(O—CH$_2$CH$_2$—)$_4$O—CH$_2$—; preferred heteroatom-containing $C_2$–$C_{24}$alkylenes are derived from ethylene glycol and correspond to the general formula (—O—CH$_2$CH$_2$O—CH$_2$CH$_2$O—CH$_2$CH$_2$—O—).

L as a $C_3$–$C_{24}$alkenylene containing one or more O atoms is derived in particular from crotonyl alcohol and isocrotonyl alcohol; such alkenyls conform in particular to the general formula (—O—CH$_2$—CH=CH—CH$_2$—O—CH$_2$—CH$_2$—).

$R_{19}$ and $R_{19}'$ in the substituent $L_1$ are preferably hydrogen or $C_1$–$C_4$alkyl, especially methyl. $L_1$ is preferably $C_2$–$C_8$alkylene or

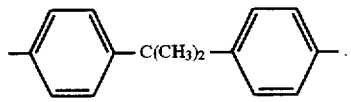

In the bridging link L the total number of C atoms (excluding any substituents $R_0$) is preferably not more than 24, especially not more than 18, for example 2 to 24, preferably 2 to 18, in particular 4 to 18.

Preferred compounds of the formula I are those in which the symbol R ortho to the Y bond is the group $R_7$ and the symbol R para to the Y bond is the OH group, and also compounds in which the symbol L is a direct bond or a bridging link of the formulae:

—CO—($C_1$-$C_{18}$alkylene)$_m$—,
—$C_1$-$C_{18}$alkylene-Q—$C_1$-$C_{18}$alkylene-,
—$C_1$-$C_{18}$alkylene-Q—$C_1$-$C_{18}$alkylene-O—,
—$C_1$-$C_{18}$alkylene-Q—$C_1$-$C_{18}$alkylene-O—CO—($C_1$-$C_{18}$alkylene)$_m$—,
—$C_1$-$C_{18}$alkylene-CH($R_0$)—O—CO—($C_1$-$C_{18}$alkylene)$_m$—,
—$C_1$-$C_{18}$alkylene-Q—$C_1$-$C_{18}$alkylene-CO—O—$C_1$-$C_{18}$alkylene,
—$C_1$-$C_{18}$alkylene-Q—$C_1$-$C_{18}$alkylene-CO—O—$C_1$-$C_{18}$alkylene-O—CO—,
—$C_1$-$C_{18}$alkylene-Q—$C_1$-$C_{18}$alkylene-CO—O—$C_1$-$C_{18}$alkylene-N($R_{11}$)—CO—,
—$C_2$-$C_{24}$alkylene containing one or more heteroatoms, or
—(CH$_2$)$_q$—CH(OR$_{12}$)—R$_{13}$—, especially those in which the symbol L is a bridging link of the formulae:

—$C_1$-$C_{18}$alkylene-Q—$C_1$-$C_{18}$alkylene-,
—$C_1$-$C_{18}$alkylene-Q—$C_1$-$C_{18}$alkylene-O—,
—$C_1$-$C_{18}$alkylene-Q—$C_1$-$C_{18}$alkylene-O—CO—($C_1$-$C_{18}$alkylene)$_m$—,
—$C_1$-$C_{18}$alkylene-CH($R_0$)—O—CO—($C_1$-$C_{18}$alkylene)$_m$—,
—$C_1$-$C_{18}$alkylene-Q—$C_1$-$C_{18}$alkylene-CO—O—$C_1$-$C_{18}$alkylene,
—$C_1$-$C_{18}$alkylene-Q—$C_1$-$C_{18}$alkylene-CO—O—$C_1$-$C_{18}$alkylene-O—CO—,
—$C_1C_{18}$alkylene-Q—$C_1$-$C_{18}$alkylene-CO—O—$C_1$-$C_{18}$alkylene-N($R_{11}$)—CO— or —CH$_2$—CH(OR$_{12}$)—R$_{13}$— and especially those in which the symbol L is the group

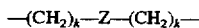

The symbol Q is preferably a direct bond.

$R_1$ and $R_2$ independently of one another are preferably $C_1$-$C_{18}$alkyl, $C_5$-$C_8$cycloalkyl, unsubstituted phenyl or phenyl substituted by $C_1$-$C_{12}$alkyl or substituted by $C_1$-$C_{12}$alkoxy, —$C_1$-$C_{18}$alkylene-COOR$_{19}$ or a group of the formula —CH$_2$—CH(OR$_{12}$)—CH$_2$O—R$_{30}$, or $R_1$ and $R_2$ together form a ring including the divalent group of the formula —(CH$_2$)$_k$—Z—(CH$_2$)$_k$— in which Z is the group —O—, —S—, —SO—, —SO$_2$—, —N(R$_{11}$)—, —OSO—O—, —O—B(R$_{20}$)—, —O—P(R$_{21}$)—O—, —N(R$_1$)—(CH$_2$)$_g$—N(R$_{11}$)—, especially those compounds in which $R_1$ and $R_2$ independently of one another are $C_1$-$C_{18}$alkyl, a group of the formula —$C_1$-$C_{12}$alkylene-COOR$_{19}$ or CH$_2$–CH(OR$_{12}$)—CH$_2$O—R$_{30}$, or $R_1$ and $R_2$ together form a ring including the divalent group of the formula —(CH$_2$)$_k$—Z—(CH$_2$)$_k$— in which Z is the group —O—, —SO— or —SO$_2$—, especially —SO$_2$—, and especially those compounds in which $R_1$ and $R_2$ together form a ring including the group —(CH$_2$)$_2$—Z—(CH$_2$)$_2$—, and also those compounds in which $R_3$ to $R_{10}$ independently of one another are H, $C_1$-$C_{18}$alkyl, $C_1$-$C_{12}$alkoxy, $C_5$-$C_8$cycloalkyl, unsubstituted phenyl or phenyl substituted by $C_1$-$C_{12}$alkyl or substituted by $C_1$-$C_{12}$alkoxy, especially those in which $R_3$ to $R_{10}$ independently of one another are H, $C_1$-$C_{18}$alkyl or $C_1C_{12}$alkoxy, and especially those in which $R_3$, $R_4$, $R_5$, $R_6$, $R_7$ and $R_{10}$ are hydrogen, $R_8$ is a branched $C_3$-$C_6$alkyl radical, especially the t-butyl or t-pentyl radical, and $R_9$ is hydrogen; and furthermore those compounds in which $R_{11}$, is H, $C_1$-$C_{18}$alkyl, unsubstituted phenyl, phenyl substituted by $C_1$-$C_{12}$alkyl or substituted by $C_1$-$C_{12}$alkoxy, or $R_{11}$, is a group —COR$_{28}$;

$R_{12}$ is H, $C_1$-$C_{18}$alkyl or —COR$_{28}$, especially hydrogen;

$R_{13}$ is a group

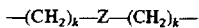

$R_{14}$ is H, $C_1$-$C_{18}$alkyl, $C_3$-$C_8$cycloalkyl, unsubstituted phenyl, phenyl substituted by $C_1$-$C_{12}$alkyl or substituted by $C_1$-$C_{12}$alkoxy, or $R_{14}$ is a 5-membered heterocyclic ring containing a hetero-atom, especially those in which $R_{14}$ is H, $C_1$-$C_{18}$alkyl or the radical of unsubstituted phenyl, or the radical of thiophene or furan, or is a $C_1$-$C_4$alkyl radical, especially the methyl radical;

then, compounds of the formula I are preferred in which $R_{15}$ to $R_{18}$ independently of one another are H, $C_1$-$C_{18}$alkyl, $C_1$-$C_{12}$alkoxy, $C_5$-$C_8$cycloalkyl, unsubstituted phenyl or phenyl substituted by $C_1$-$C_{12}$alkyl or substituted by $C_1$-$C_{12}$alkoxy, especially those in which $R_{15}$ to $R_{18}$ independently of one another are H, $C_1$-$C_{18}$alkyl or $C_1$-$C_{12}$alkoxy and especially those in which $R_{15}$ and $R_{17}$ are hydrogen, $R_{16}$ is a branched $C_3$-$C_6$alkyl radical, especially the t-butyl or t-pentyl radical, $R_{18}$ is hydrogen or a $C_1$-$C_4$alkyl radical, especially hydrogen or methyl, and $R_{19}$ is $C_1$-$C_{18}$alkyl, unsubstituted phenyl or phenyl substituted by $C_1$-$C_{12}$alkyl or substituted by $C_1$-$C_{12}$alkoxy, especially $C_1$-$C_{18}$alkyl; $R_{20}$ and $R_{21}$ are in particular $C_1$-$C_{18}$alkyl or unsubstituted phenyl; $R_{22}$ and $R_{23}$ independently of one another are hydrogen, $C_1$-$C_{18}$alkyl, $C_5$-$C_8$cycloalkyl, unsubstituted phenyl, phenyl substituted by $C_1$-$C_{12}$alkyl or substituted by $C_1$-$C_{12}$alkoxy, or $R_{22}$ and $R_{23}$ are (CH$_2$)$_n$COOR$_{18}$ and are especially hydrogen or $C_1$-$C_{18}$alkyl;

$R_{24}$ to $R_{27}$ independently of one another are hydrogen, $C_1$-$C_{18}$alkyl, $C_1$-$C_{12}$alkoxy, $C_5$-$C_8$cycloalkyl, unsubstituted phenyl, phenyl substituted by $C_1$-$C_{12}$alkyl or substituted by $C_1$-$C_{12}$alkoxy, or $R_{24}$ to R27 are a group —$C_1$-$C_{12}$alkylene-COOR$_{29}$, especially H, $C_1$-$C_{18}$alkyl, $C_1$-$C_{12}$alkoxy or —$C_1$-$C_{12}$alkylene-COOR$_{29}$, and then preferred compounds are those in which $R_{28}$ and $R_{29}$ independently of one another are $C_1$-$C_{18}$alkyl, $C_5$-$C_8$cycloalkyl, unsubstituted phenyl, phenyl substituted by $C_1$-$C_{12}$alkyl or substituted by $C_1$-$C_{12}$alkoxy, or else $R_{29}$ is a group of the formula

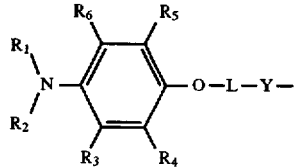

provided that $R_{25}$ is the group —$C_1$-$C_{12}$alkylene-COOR$_{29}$, in which Y is a direct bond, and especially those in which $R_{29}$ is $C_1$-$C_{18}$alkyl or, where $R_{25}$ is a group —$C_1$-$C_{12}$alkylene-COOR$_{29}$, is a group of the formula

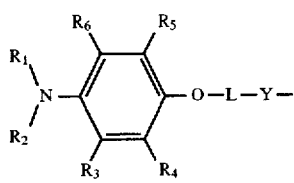

in which Y is a direct bond;
and in which m is zero or an integer from 1 to 6, and especially zero, 1 or 2; q is an integer from 1 to 11, especially 1, and k is 2 and Z is the group —O— or —SO$_2$—.

Of particular interest on account of their very good properties in colour-photographic recording materials are compounds of the formula I in which the symbol R ortho to the Y bond is a group R$_7$ and the symbol R para to the Y bond is the OH group, and in which R$_{10}$ is H, C$_1$–C$_{18}$alkenyl, C$_1$–C$_{12}$alkoxy, C$_5$–C$_8$cycloalkyl, unsubstituted or substituted aryl, and halogen, where R$_8$ and R$_{10}$ independently of one another may also be a group of the formula

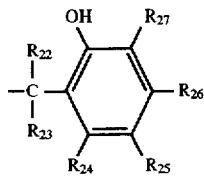

and all remaining symbols are as defined in claim 1, and then those compounds of the formula I in which R$_1$ and R$_2$ form a ring including the group

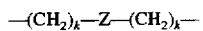

where Z has the definition indicated at the outset, especially the group —O— or —SO$_2$—, and each k is an integer from 1 to 3;

R$_3$, R$_4$, R$_5$ and R$_6$ independently of one another are hydrogen or a C$_1$–C$_{18}$alkyl radical or an aryl radical which is unsubstituted or is substituted by C$_1$–C$_{12}$alkyl or C$_1$–C$_{12}$alkoxy, and in particular are each hydrogen;

L is a group

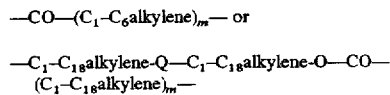

in which Q is a direct bond;
Y is a direct bond or a group of the formula

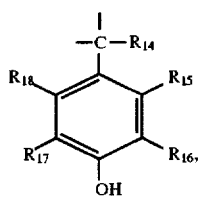

in which R$_{14}$ is hydrogen, a C$_1$–C$_{18}$alkyl group or an aryl radical which is unsubstituted or is substituted by C$_1$–C$_{12}$alkyl or C$_1$–C$_{12}$alkoxy, or is a heterocyclic ring, especially a straight-chain C$_1$–C$_4$alkyl, R$_{15}$, R$_{16}$, R$_{17}$ and R$_{18}$ independently of one another are hydrogen, C$_1$–C$_{18}$alkyl or an aryl radical which is unsubstituted or substituted by C$_1$–C$_{12}$alkyl or C$_1$–C$_{12}$alkoxy, and in particular R$_{15}$ is hydrogen, R$_{16}$ is a branched C$_1$C$_4$alkyl group, R$_{17}$ and R$_{18}$ are each hydrogen, R$_7$, R$_9$ and R$_{10}$ are each hydrogen, and R$_8$ is a C$_1$–C$_{18}$alkyl radical, especially a branched C$_1$–C$_4$alkyl group.

The compounds of the general formula I can be prepared by known methods, for example by
a) if the symbol L is the —CO— or —CO—C$_1$–C$_{18}$alkylene group reacting a compound of the general formula II

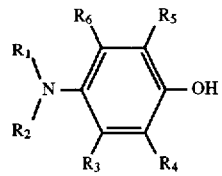

with a compound of the general formula III

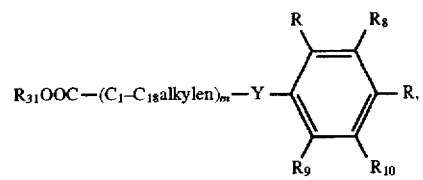

or b) if the symbol L is the group

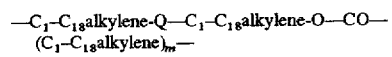

reacting a compound of the general formula IV

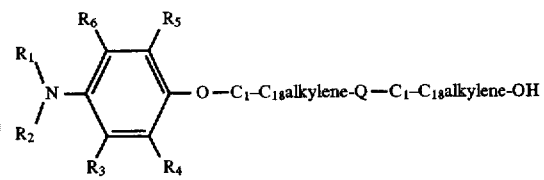

with a compound of the general formula III

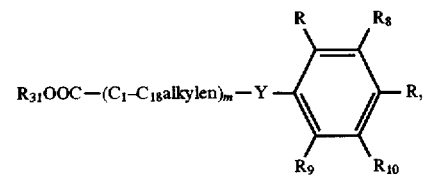

all these reactions expediently being carried out at elevated temperature in a water-insoluble organic solvent under an inert gas, and the symbols being as defined below formula I and R$_{31}$ being a C$_1$–C$_6$alkyl radical.

The phrase at elevated temperature refers in this context to a temperature range of preferably 50° to 200° C., for example 120° to 170° C., the preferred temperature range being from 140° to 150° C.

The remaining compounds of the formula I can be prepared analogously by means of customary esterification, transesterification or etherification reactions. Particular examples of suitable water-insoluble, organic solvents are aromatic hydrocarbons, such as toluene and xylene, or mixtures thereof.

The reactions are, furthermore, expediently carried out under an inert gas atmosphere, especially under a nitrogen atmosphere, and in the presence of a catalyst, for example an organotin compound such as dibutyltin oxide.

The compounds of the formulae II and III employed as starting materials are known and can be prepared by known methods, for example in accordance with JP-A-04 182 468 and O. Mauz., Ann. Chem. 1974, p. 345.

The symbol $R_{31}$ in the starting materials of the formula III is a $C_1$–$C_6$alkyl radical, especially an unbranched alkyl radical, and in particular a $C_1$–$C_3$alkyl radical, especially the $CH_3$ radical.

Alternatively, the compounds of the formula II or IV can also be reacted with corresponding acid chlorides (compounds of the formula III where —$OR_{31}$=Cl), likewise affording the desired esters. In this case the reaction is expediently carried out in the presence of a HCl acceptor, for example an amine, preferably a tertiary amine such as triethylamine, for instance. In this case it is possible to operate at temperatures preferably in the range from 25° to 200° C., especially from 40° to 150° C.

The starting materials of formula IV are novel and are a further subject of the invention. They are obtained, for example, by reacting a compound of the formula II with a haloalkyl alcohol of the formula VI

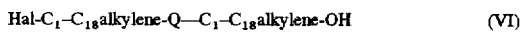

Hal-$C_1$-$C_{18}$alkylene-Q—$C_1$-$C_{18}$alkylene-OH               (VI)

in which Hal is halogen, especially fluorine, chlorine, iodine and, in particular, bromine, in an organic solvent at a temperature of from about 70° C. to 100° C. Examples of suitable solvents are those containing at least one —OH, —Oalkyl, —COOH, —COOalkyl, —COalkyl or —CON(alkyl)$_2$ group; those mentioned in particular are aliphatic monoalcohols, such as methanol, ethanol, 1-butanol and methoxypropyl alcohol; aliphatic dialcohols, such as ethylene glycol; ketones, such as methyl ethyl ketone and methyl isobutyl ketone, and also ethers, such as butyl methyl ether. However, it is also possible to use mixtures of these solvents.

The compounds of the formula I can be used individually or in mixtures with one another as stabilizers for colour-photographic recording materials. These materials are predominantly papers or films comprising three photosensitive layers: the yellow layer, the magenta layer and the cyan layer. These layers are gelatine layers containing at least one silver halide and a dye coupler, and possible further additives as well. The compounds of the formula I are added to one such gelatine layer.

The compounds of the formula I are expediently employed in a quantity of up to 1 g/m$^2$, preferably from 10 to 300 mg/m$^2$, per colour layer. The addition can be made to one or two or all three colour silver layers. Addition to the magenta layer is of particular importance. The layers comprise the sensitized silver halide and the respective colour coupler. The layers may additionally comprise further stabilizers and/or other additives.

The novel compounds are particularly effective as stabilizers for magenta couplers and magenta dyes. It is surprising that the addition of one or more compounds of the general formula I to a colour-photographic recording material comprising a magenta coupler not only results in enhanced photostability of the magenta coupler and colour image and prevents the magenta colour image fading as a result of the effect of light during long-term storage, even at elevated temperatures and humidity, but also prevents white sections of the image area yellowing under the effect of light when they are subject to light, heat or humidity, and it is also surprising that there is no unwanted change in the colour of the colour image.

This is all the more surprising since, in comparison with yellow dyes and cyan dyes, magenta dyes fade more rapidly under the action of light, and since the problem of yellowing is more acute with magenta couplers than with yellow couplers and cyan couplers.

The attempt to develop colour-photographic recording materials even more quickly and in doing so to use chemicals which are easier to handle and less polluting has led to considerable restrictions in the choice of components of the system. Thus the silver halide emulsions used are those based substantially or exclusively on silver chloride, thereby reducing the development time. It has also been found that developer systems largely or totally devoid of benzyl alcohol can be used without any reduction in the colour density. This makes it possible to produce developer concentrates from fewer constituents, with shorter mixing times and reduced toxicity of the used developer. In order to achieve this aim of shortening the development time and reducing the amount of benzyl alcohol, the following additives may be used:

a) N-substituted hydroxylamines as antioxidants in place of the customary hydroxylamines, b) development accelerators, for example 1-aryl-3-pyrazolones, hydrazine derivatives, quaternary ammonium and phosphonium compounds, or polyoxyalkylene compounds, c) triethanolamine as tar inhibitor, d) lithium salts, for example those of polystyrenesulfonates, e) aromatic polyhydroxy compounds, for example sodium 5,6-dihydroxy-1,2,4-benzenetrisulfonate.

The compounds of the formula I can also be used in those rapidly developable systems, such as in photographic layers based on silver chloride emulsions, and those systems which are developed entirely or largely without benzyl alcohol.

The invention therefore relates, furthermore, to a novel colour-photographic recording material comprising a magenta coupler and, as stabilizer, a O-phenol-substituted amino-phenol derivative of the formula I.

The novel compounds of the formula I can be used for all kinds of photosensitive material. For example, they can be employed for colour paper, colour reversal paper, direct-positive colour material, colour negative film, colour positive film, colour reversal film etc. They are preferably used, inter alia, for photosensitive colour material which comprises a reversal substrate or which forms positives.

Colour-photographic recording materials such as those described in U.S. Pat. No. 4 518 686 can also be stabilized with great success.

Colour-photographic recording materials normally comprise, on a base, a blue-sensitive and/or a green-sensitive and/or a red-sensitive silver halide emulsion layer and, if desired, a protective layer, a layer containing a UV absorber being arranged above the topmost silver halide emulsion layer.

In a further embodiment, the novel material comprises a layer containing a compound of the formula (I), which is arranged between the green-sensitive and the red-sensitive silver halide emulsion layer, it being possible for a further layer containing a compound of the formula (I) to be arranged above the topmost silver halide emulsion layer.

Good results are also obtained if the compound of the formula (I) is additionally present in the red-sensitive silver halide emulsion layer.

Preference extends to photographic recording materials which have a layer comprising a compound of the formula (I) above the topmost silver halide emulsion layer and/or between the green-sensitive and the red-sensitive silver halide emulsion layer.

Furthermore, it may be advantageous for all or some of the said layers which may contain a compound of the formula I to have a compound of the formula (I) and/or another compound of the formula I which is dispersible in aqueous gelatine, with the proviso that a compound of the formula (I) must be present at least in one layer.

The novel material preferably includes gelatine interlayers between the silver halide emulsion layers.

Preferred photographic recording materials are those in which the silver halide present in the blue-, green- and/or red-sensitive layer is silver chloride bromide of which at least 90 mol % consists of silver chloride.

Other preferred photographic recording materials are those where the sequence of the silver halide emulsion layers is blue-sensitive, green-sensitive and red-sensitive silver halide emulsion layer.

Yellow couplers which can be used in the novel material are preferably compounds of the formula A $$R_1-CO-CH(Q)-CO-NHR_2, \quad (A)$$

in which $R_1$ is alkyl or aryl, $R_2$ is aryl and Q is hydrogen or a group which can be eliminated by reaction with the oxidized developer.

One group of yellow couplers comprises those compounds of the formula A in which $R_1$ is t-butyl and $R_2$ is a group of the formula

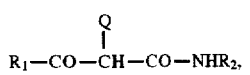

in which $R_3$ is hydrogen, halogen, alkyl or alkoxy and $R_4$, $R_5$ and $R_6$ are hydrogen, halogen, alkyl, alkenyl, alkoxy, aryl, carboxyl, alkoxycarbonyl, a carbamoyl group, a sulfonyl or sulfamoyl group, an alkylsulfonamino group, acylamino group, ureido group or amino group.

Preferably, $R_3$ is chlorine, $R_4$ and $R_5$ are hydrogen and $R_6$ is an acylamino group. This also includes the compounds of the formula

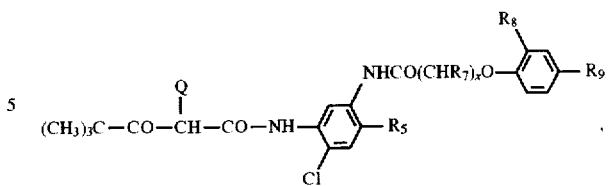

in which x is 0–4, $R_7$ is hydrogen or alkyl and $R_8$ and $R_9$ are alkyl.

Another group of yellow couplers conforms to the formula B

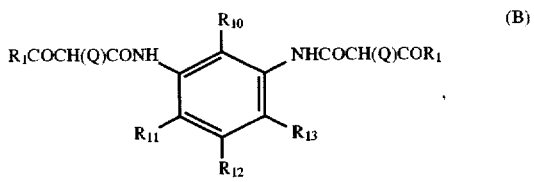

(B)

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, a carbamoyl group, a sulfonyl group, a sulfamoyl group, sulfonamido group, acylamino group, ureido group or amino group and $R_1$ and Q are as defined above.

This group includes compounds of the formula B in which $R_1$ is t-butyl, $R_{10}$ is chlorine, $R_{11}$, and $R_{13}$ are hydrogen and $R_{12}$ is alkoxycarbonyl.

In the compounds of the formulae A and B the leaving group Q can be hydrogen or is a heterocyclic group

in which $R_{14}$ is a divalent organic group which supplements the ring to make up a 4–7-membered ring, or Q is a group $-OR_{15}$ in which $R_{15}$ is alkyl, aryl, acyl or a heterocyclic radical.

Typical examples of customary yellow couplers are the compounds of the following formulae:

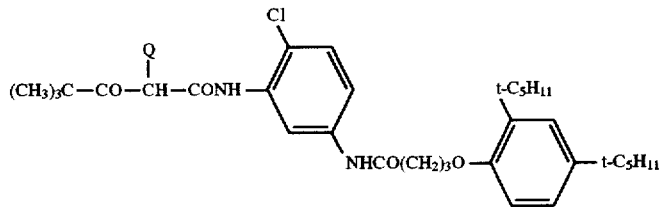

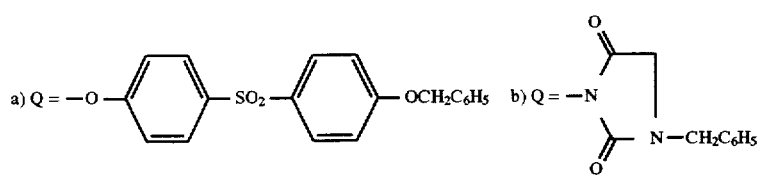

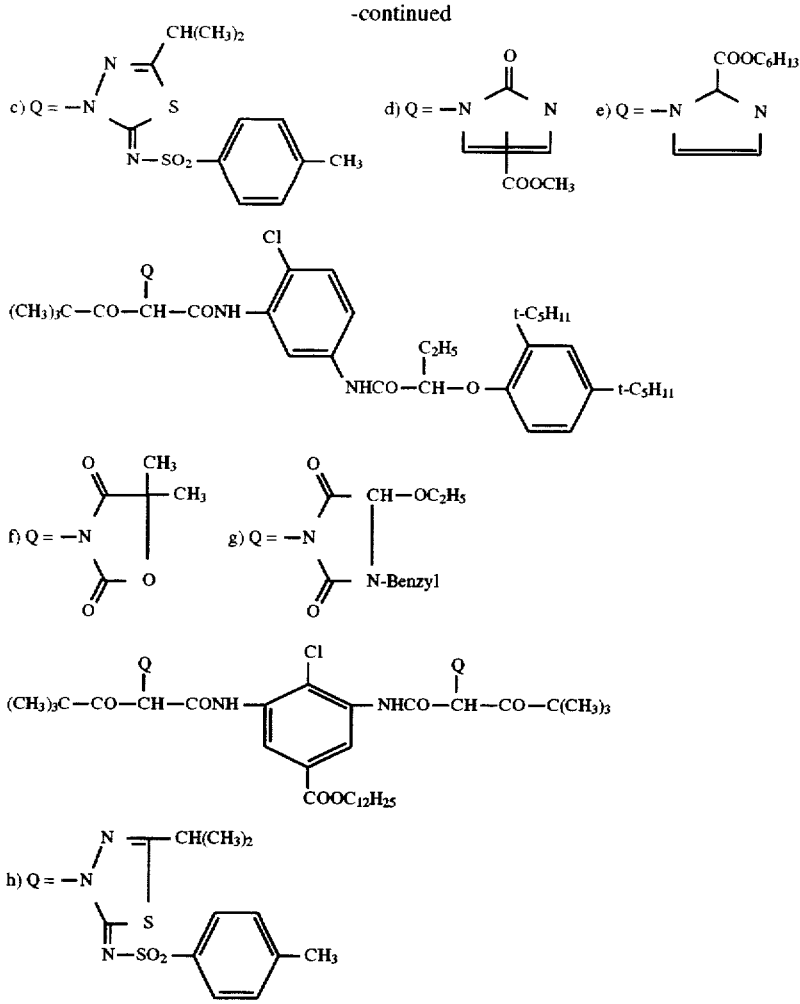
Further examples of yellow couplers are given in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, in DE-A 1,547,868, 2,057,941, 2,162,899, 2,163,813, 2,213,461, 2,219,917, 2,261,361, 2,261,362, 2,263,875, 2,329,587, 2,414,006 and 2,422,812, in GB-A 1,425,020 and 1,077,874 and in JP-A-88/123,047 and in EP-A-447,969.
The yellow couplers are customarily used in an amount of 0.05–2 mol and preferably 0.1–1 mol per mole of silver halide.
Typical and preferred yellow couplers conform to the formulae:
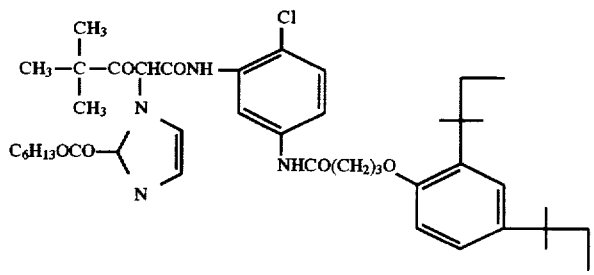
(Y-1)

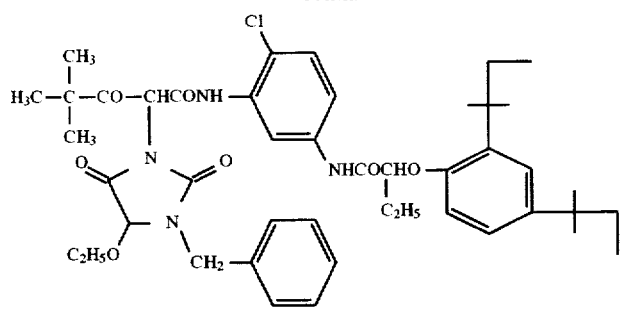
(Y-2)
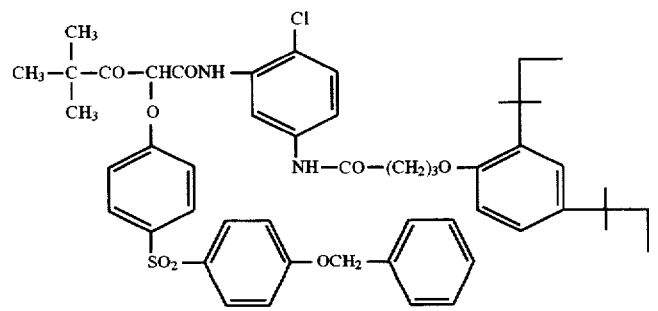
(Y-3)
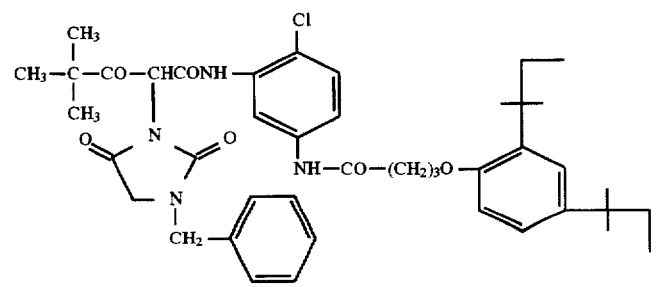
(Y-4)
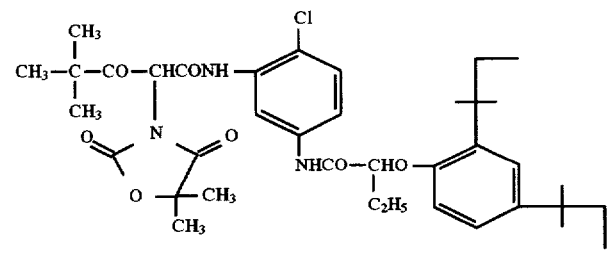
(Y-5)
$-\!\!\!+\!\!\!-$ = $-C(CH_3)_2C_2H_5$
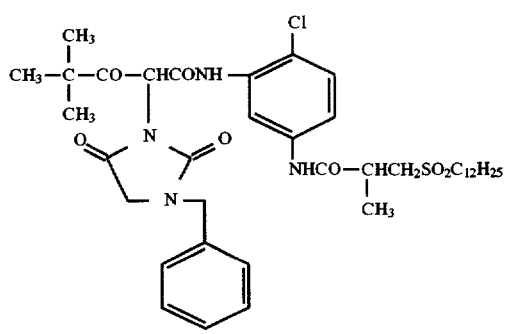
(Y-6)

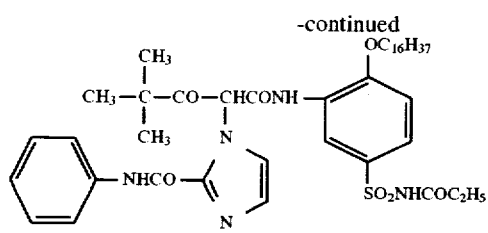
(Y-7)

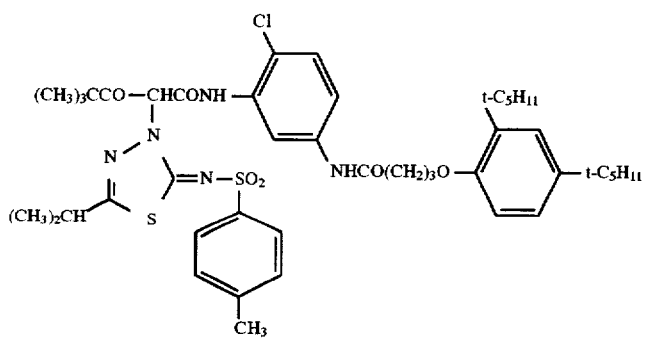
(Y-8)

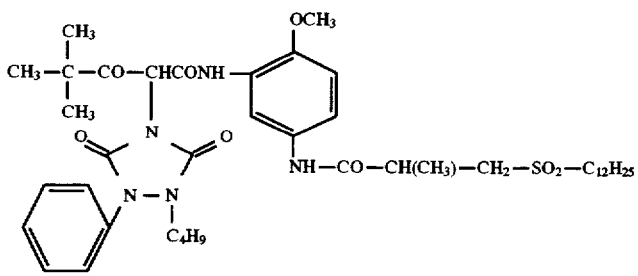
(Y-9)

Magenta couplers may, for example, be simple 1-aryl-5-pyrazolones or may be pyrazole derivatives which are fused with 5-membered heterocyclic rings, examples being imidazopyrazoles, pyrazolopyrazoles, pyrazolotriazoles or pyrazolotetrazoles.

One group of magenta couplers comprises 5-pyrazolones of the formula C

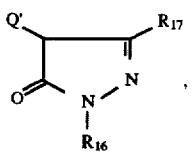
(C)

as are described in British Patent 2,003,473. In this formula, $R_{16}$ is hydrogen, alkyl, aryl, alkenyl or a heterocyclic group. $R_{17}$ is hydrogen, alkyl, aryl, a heterocyclic group, an ester group, alkoxy group, alkylthio group, carboxyl group, arylamino group, acylamino group, (thio)urea group, (thio)carbamoyl group, guanidino group or sulfonamido group.

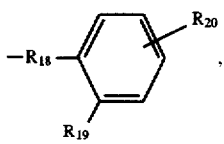

in which $R_{18}$ is imino, acylamino or ureido, $R_{19}$ is hydrogen, halogen, alkyl or alkoxy, $R_{20}$ is hydrogen, alkyl, acylamino, carbamoyl, sulfamoyl, sulfonamido, alkoxycarbonyl, acyloxy or a urethane group.

If Q' is hydrogen, then the magenta coupler is tetraequivalent in relation to the silver halide.

Typical examples of this type of magenta coupler are compounds of the formula

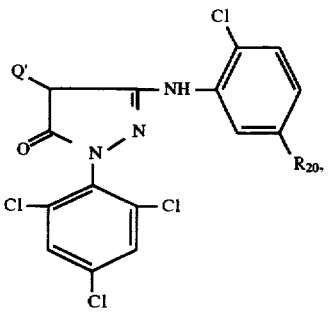

in which $R_{20}$ is as defined above and Q', as described above, is a leaving group. These compounds are preferably present in the novel material.

Further examples of such tetraequivalent magenta couplers are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and in JP-A-89/309,058.

If Q' in formula C is not hydrogen but a group which is eliminated in reaction with the oxidized developer, then the magenta coupler is diequivalent. In this case Q may for example be halogen or a group which is attached via O, S or N to the pyrazole ring. Diequivalent couplers of this kind give rise to a higher colour density and are more reactive with respect to the oxidized developer than are the corresponding tetraequivalent magenta couplers.

Examples of diequivalent magenta couplers are described in U.S. Pat. Nos. 3,006,579, 3,419,391, 3,311,476, 3,432,521, 3,214,437, 4,032,346, 3,701,783, 4,351,897, 3,227,554, in EP-A-133,503, DE-A-2,944,601, JP-A-78/34044, 74/53435, 74/53436, 75/53372 and 75/122935.

Typical and preferred magenta couplers conform to the formulae

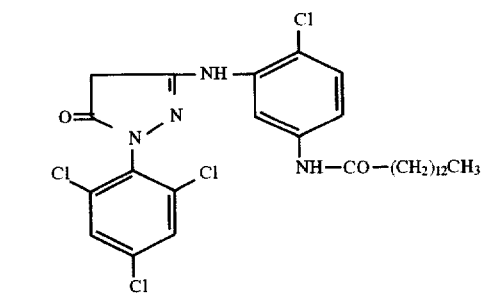
(M-1)

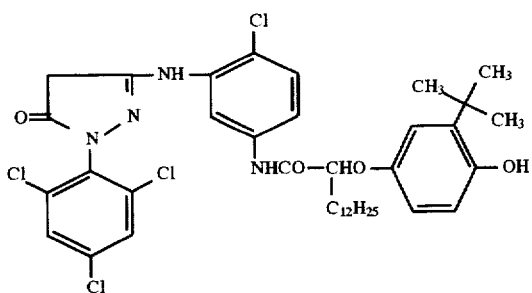
(M-2)

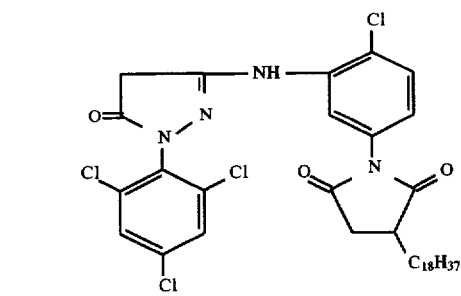
(M-3)

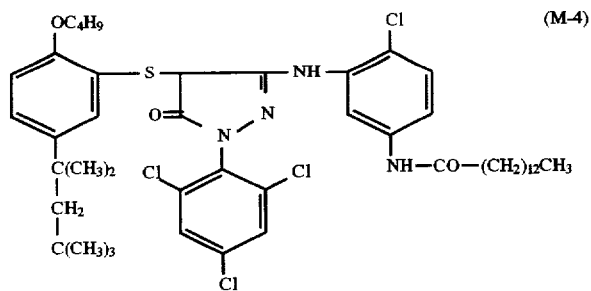
(M-4)

It is possible for 2 pyrazolone rings to be linked via a divalent Q', giving so-called biscouplers. These are described, for example, in U.S. Pat. No. 2,632,702, U.S. Pat. No. 2,618,864, GB-A-968,461, GB-A-786,859, JP-A-76/37646, 59/4086, 69/16110, 69/26589, 74/37854 and 74/29638. Y is preferably an O-alkoxyarylthio group.

As mentioned above, the magenta couplers used can also be pyrazoles fused with 5-membered heterocycles, and are then known as pyrazoloazoles. Their advantages over simple pyrazoles are that they possess colours of greater formalin resistance and have purer absorption spectra.

Magenta couplers of the pyrazoloazole type which are likewise preferred may be represented by the formula

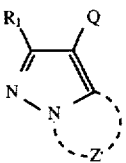

in which $R_1$ is hydrogen or a substituent, Z represents the non-metallic atoms necessary to complete a 5-membered ring containing 2 or 3 nitrogen atoms, which ring may be substituted, and Q is hydrogen or a leaving group.

Of these compounds, preference is given to magenta couplers of the formulae

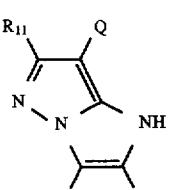
(M-a)

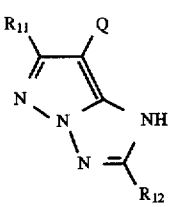
(M-b)

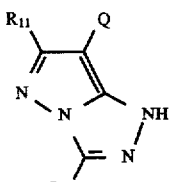
(M-c)

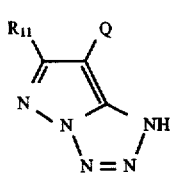
(M-d)

$R_{11}$, $R_{12}$ and $R_{13}$ independently of one another are, for example, hydrogen, halogen, a group of the formula —$CR_3$ in which the radicals $R_1$ independently of one another, are hydrogen or alkyl, or aryl, heterocyclyl, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclyloxy, azo, acyloxy, carbamoyloxy, silyloxy, aryloxycarbonylamino, imido, heterocyclic ring-thio, sulfinyl, phosphonyl, aryloxycarbonyl, acyl or azolyl, and preferably hydrogen; halogen (e.g. chlorine, bromine), a group of the formula —$CR_3$ in which the radicals R independently of one another are hydrogen or alkyl, or aralkyl, alkenyl, alkynyl, cycloalkyl or cycloalkenyl, and particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy) dodecaneamido)phenyl)propyl, 2-ethoxytridecyl, trifluoromethyl, cyclopentyl, 3-(2,4-di-t-amylphenoxy) propyl); aryl (e.g. phenyl, 4-t-butylphenyl, 2,4-di-t-amylphenyl, 4-tetradecanamidophenyl); heterocyclyl (e.g.

2-furyl, 2-thienyl, 2-pyrimidinyl, 2-benzothiazolyl); cyano; hydroxyl, nitro; carboxyl; amino; alkoxy (e.g. methoxy, ethoxy, 2-methoxyethoxy; 2-dodecylethoxy, 2-methanesulfonylethoxy); aryloxy (e.g. phenoxy, 2-methylphenoxy, 4-t-butylphenoxy, 3-nitrophenoxy, 3-t-butyloxycarbamoylphenoxy, 3-methoxycarbamoyl); acylamino (e.g. acetamido, benzamido, tetradecaneamido, 2-(2, 4-di-t-amylphenoxy)butaneamido, 4-(3-t-butyl-4-hydroxyphenoxy)butaneamido, 2-(4-(4-hydroxyphenylsulfonyl)phenoxy)dodecaneamido); methylbutylamino); anilino (e.g. phenylamino, 2-chloroanilino, 2-chloro-5-tetradecaneaminoanilino, 2-chloro-5-dodecyloxycarbonylanilino, N-acetylanilino, 2-chloro-5-(alpha-(3-t-butyl-4-hydroxyphenoxy) dodecaneamidoanilino); ureido (e.g. phenylureido, methylureido, N,N-dibutylureido); sulfamoylamino (e.g. N,N-dipropylsulfamoylamino, N-methyl-N-decylsulfamoylamino); alkylthio (e.g. methylthio, octylthio, tetradecylthio, 2-phenoxyethylthio, 3-phenoxypropylthio, 3-(4-t-butylphenoxy)propylthio); arylthio (e.g. phenylthio, 2-butoxy-5-t-octylphenylthio, 3-pentadecylphenylthio, 2-carboxyphenylthio, 4-tetradecaneamidophenylthio); alkoxycarbonylamino (e.g. methoxycarbonylamino, tetradecyloxycarbonylamino); sulfonamido (e.g. methanesulfonamido, hexadecanesulfonamido, benzenesulfonamido, p-toluenesulfonamido, octadecanesulfonam ido, 2-methyloxy-5-t-butylbenzenesulfonamido); carbamoyl (e.g. N-ethylcarbamoyl, N,N-dibutylcarbamoyl, N-(2-dodecyloxyethyl)carbamoyl, N-methyl-N-dodecylcarbamoyl, N-(3-(2,4-di-t-amylphenoxy)propyl) carbamoyl); sulfamoyl (e.g. N-ethylsulfamoyl, N,N-dipropylsulfamoyl, N-2(-dodecyloxyethyl)sulfamoyl, N-ethyl-N-dodecylsulfamoyl, N,N-diethylsulfamoyl); sulfonyl (e.g. methanesulfonyl, octanesulfonyl, benzenesulfonyl, toluenesulfonyl); alkoxycarbonyl (e.g. methoxycarbonyl, butoxycarbonyl, dodecyloxycarbonyl, octadecyloxycarbonyl); heterocyclic ring-oxy (e.g. 1-phenyltetrazole-5-oxy, 2-tetrahydropyranyloxy); azo (e.g. phenylazo, 4-methoxyphenylazo, 4-pivaloylaminophenylazo, 2-hydroxy-4-propanoylphenylazo); acyloxy (e.g. acetoxy); carbamoyloxy (e.g. N-methylcarbamoyloxy, N-phenylcarbamoyloxy); silyloxy (e.g. trimethylsilyloxy, dibutylmethylsilyloxy); aryloxycarbonylamino (e.g. phenoxycarbonylamino); imido (e.g. N-succinimido, N-phthalimido, 3-octadecenylsuccinimido); heterocyclic ring-thio (e.g. 2-benzothiazolylthio, 2,4-diphenyloxy-1,3,5-triazole-6-thio, 2-pyridylthio); sulfinyl (e.g. dodecanesulfinyl, 3-pentadecylphenylsulfinyl, 3-phenoxypropylsulfinyl); phosphonyl (e.g. phenoxyphosphonyl, octyloxyphosphonyl, phenylphosphonyl); aryloxycarbonyl (e.g. phenoxycarbonyl); acyl (e.g. acetyl, 3-phenylpropanoyl, benzoyl, 4-dodecyloxybenzoyl); azolyl (e.g. imidazolyl, pyrazolyl, 3-chloropyrazol-1-yl).

These substituents may be substituted further, for example by halogen or by an organic radical attached via a C, O, N or S atom.

The preferred groups $R_{11}$ are alkyl, aryl, alkoxy, aryloxy, alkylthio, ureido, urethane and acyl-amino groups.

$R_{12}$ may be as defined for $R_{11}$, and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, heterocyclyl, alkoxy, aryloxy, alkylthio, arylthio, alkoxycarbonyl, carbamoyl or acyl, preferably alkyl, aryl, heterocyclyl, alkylthio or arylthio.

Q is hydrogen or a leaving group such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered nitrogen-containing heterocyclic radical, imido and arylazo. These groups may be further substituted as indicated for $R_{11}$.

Q is preferably halogen (for example fluorine, chlorine, bromine); alkoxy (e.g. ethoxy, dodecyloxy, methoxyethylcarbamoylmethoxy, carboxypropyloxy, methylsulfonylethoxy, ethoxycarbonylmethoxy); aryloxy (e.g. 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy); acyloxy (e.g. acetoxy, tetradecanoyloxy, benzoyloxy); alkyl- or arylsultonyloxy (e.g. methanesulfonyloxy, toluenesulfonyloxy); acylamino (e.g. dichloroacetylamino, heptafluorobutyrylamino); alkyl- or arylsulfonamido (e.g. methanesulfonamido, trifluoromethanesulfonamido, p-toluenesulfonylamido); alkoxycarbonyloxy (e.g. ethoxy-carbonyloxy, benzyloxycarbonyloxy); aryloxycarbonyloxy (e.g. phenoxycarbonyloxy); alkyl-, aryl- or heterocyclyl-S—(e.g. dodecylthio, 1-carboxydodecylthio, phenylthio, 2-butoxy-5-t-octylphenylthio, tetrazolylthio); carbamoylamino (e.g. N-methylcarbamoylamino, N-phenylcarbamoylamino); 5- or 6-membered nitrogen-containing ring (e.g. imidazolyl, pyrazolyl, triazolyl, tetrazolyl, 1,2-dihydro-2-oxo-1-pyridyl); imido (e.g. succinimido, hydantoinyl); arylazo (e.g. phenylazo, 4-methoxyphenylazo).

Q may alternatively form corresponding bis-compounds by condensation of 4 equivalents of coupler with an aldehyde or ketone. Furthermore, Q may contain photographically active groups, such as development inhibitors or development accelerators. Q is preferably halogen, alkoxy, aryloxy, alkyl- or arylthio, or a 5- or 6-membered nitrogen-containing heterocyclic group which is bonded to the coupling site via a nitrogen atom.

Pyrazolotetrazoles are described in JP-A-85/33552; pyrazolopyrazoles in JP-A-85/43,695; pyrazoloimidazoles in JP-A-85/35732, JP-A-86/18949 and U.S. Pat. No. 4,500, 630; pyrazolotriazoles in JP-A-85/186,567, JP-A-86/47957, JP-A-85/215,687, JP-A-85/197,688, JP-A-85/172,982, EP-A-1 19,860, EP-A-173,256, EP-A-178,789, EP-A-178, 788 and in Research Disclosure 84/24,624.

Further pyrazoloazole magenta couplers are described in: JP-A-86/28,947, JP-A-85/140,241, JP-A-85/262,160, JP-A-85/213,937, JP-A-87/278,552, JP-A-87/279,340, JP-A-88/100,457, EP-A-177,765, EP-A-176,804, EP-A-170,164, EP-A-164,130, EP-A-178,794, DE-A-3,516,996, DE-A-3, 508,766 and Research Disclosure 81/20919, 84/24531 and 85/25758.

Suitable examples of such couplers are:

(M-5)

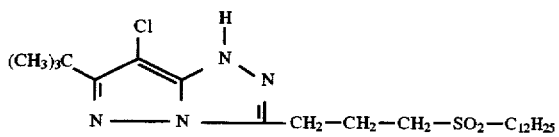

-continued
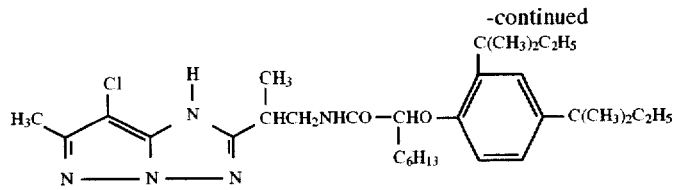
(M-6)
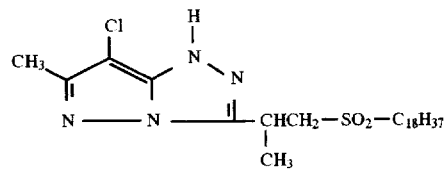
(M-7)
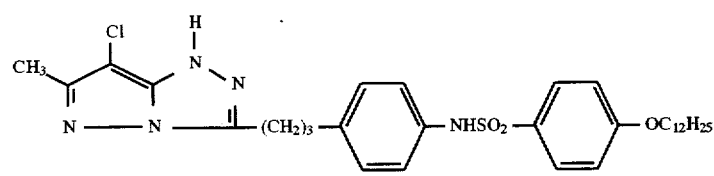
(M-8)
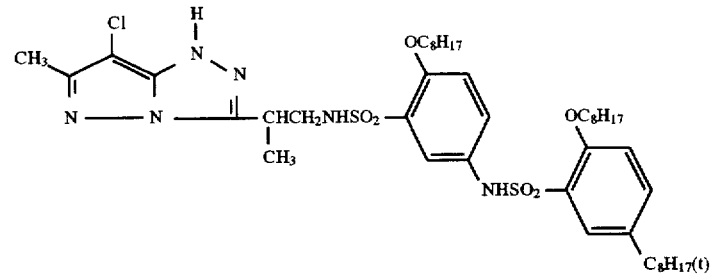
(M-9)
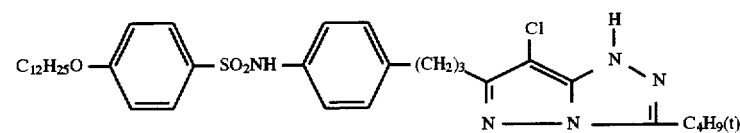
(M-10)
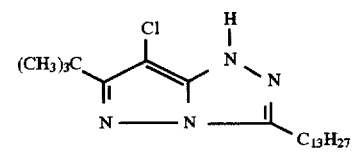
(M-11)
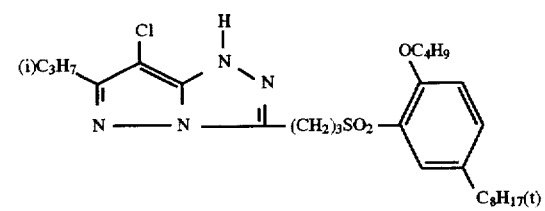
(M-12)
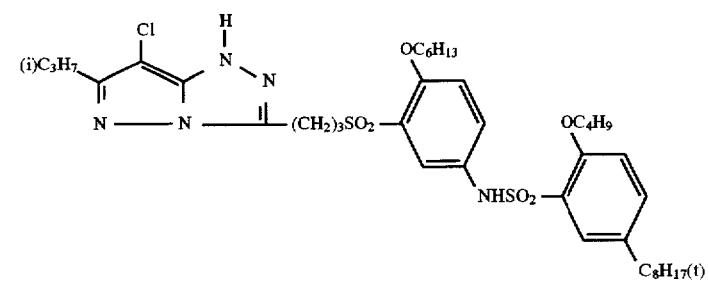
(M-13)

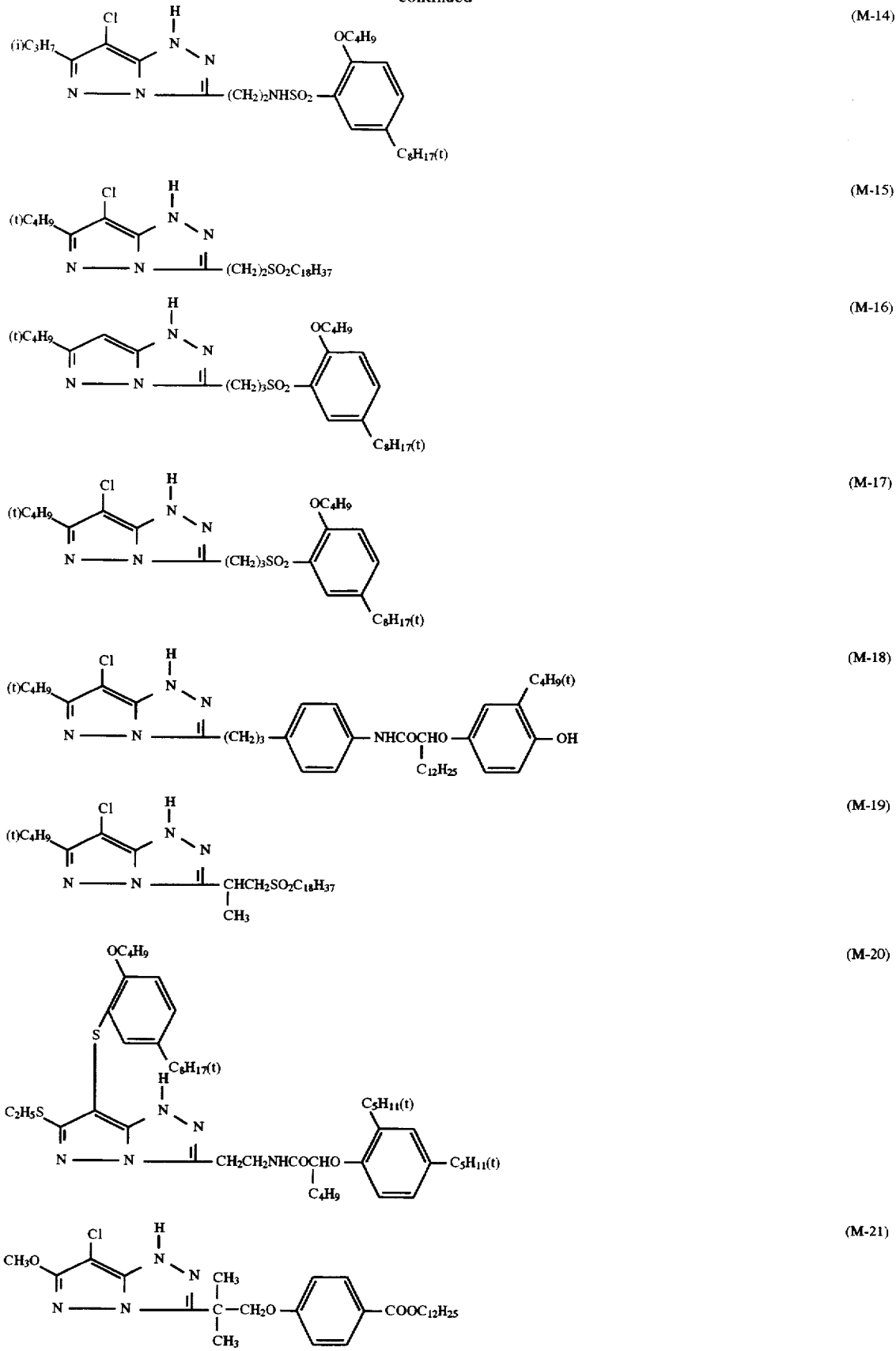

-continued
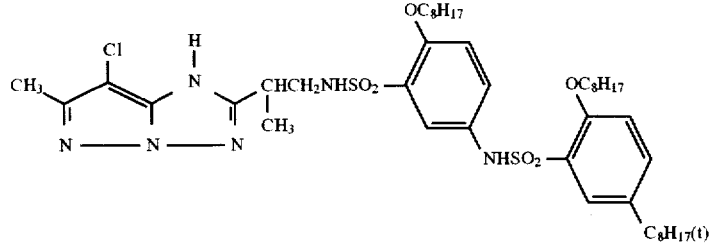
(M-22)
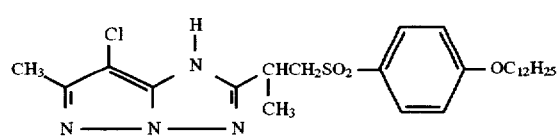
(M-23)
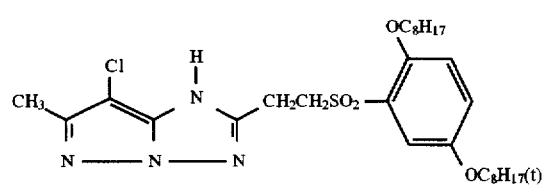
(M-24)
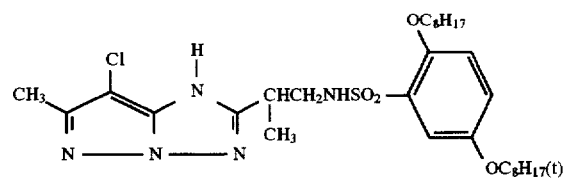
(M-25)
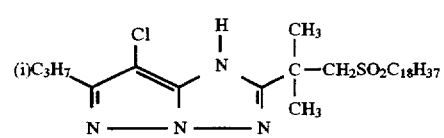
(M-26)
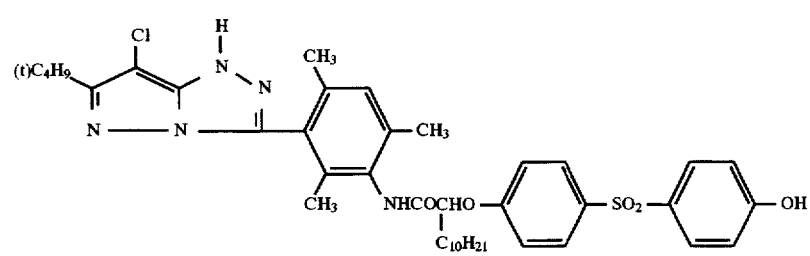
(M-27)
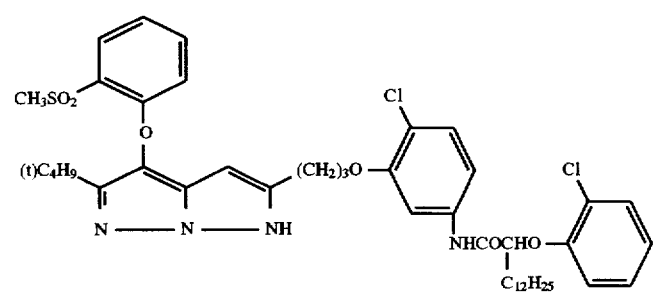
(M-28)
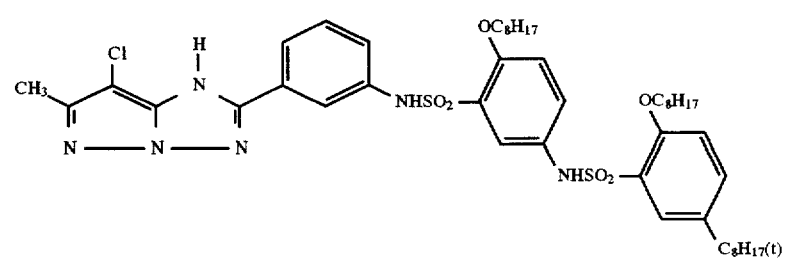
(M-29)

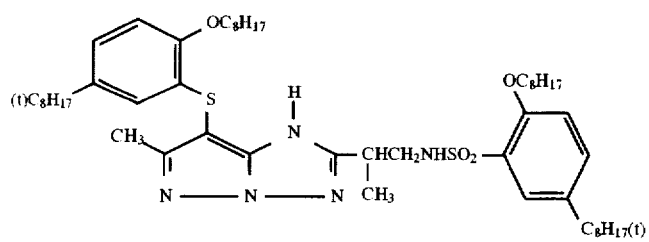 (M-30)
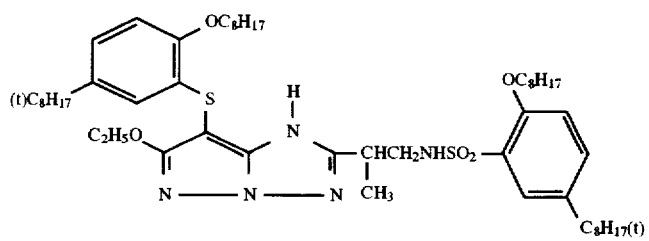 (M-31)
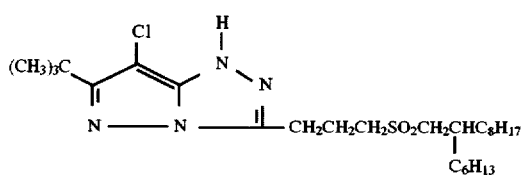 (M-32)
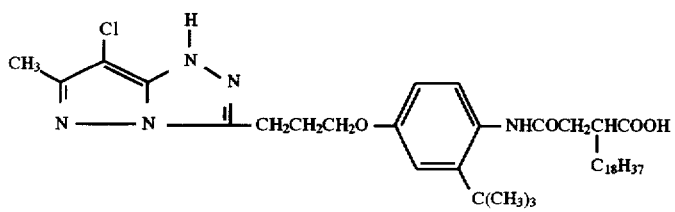 (M-33)
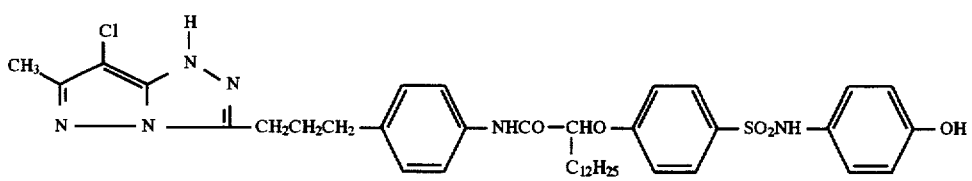 (M-34)
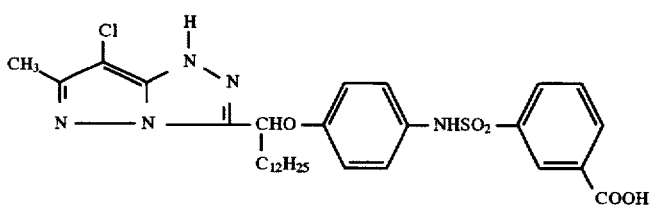 (M-35)
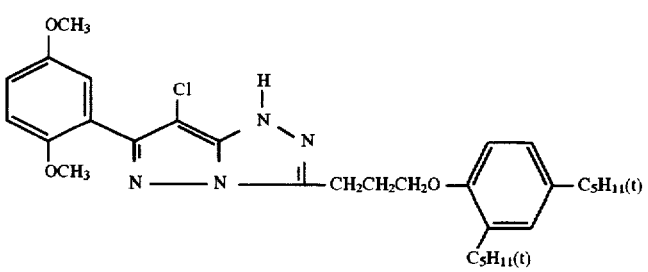 (M-36)

(M-37)
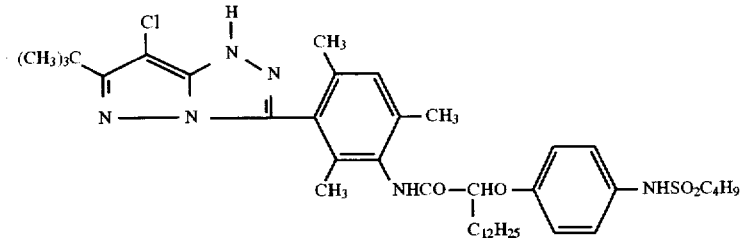
(M-38)
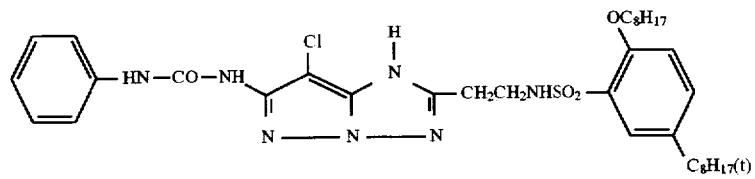
(M-39)
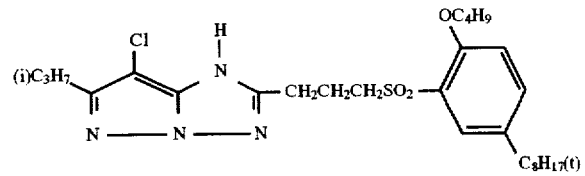
(M-40)
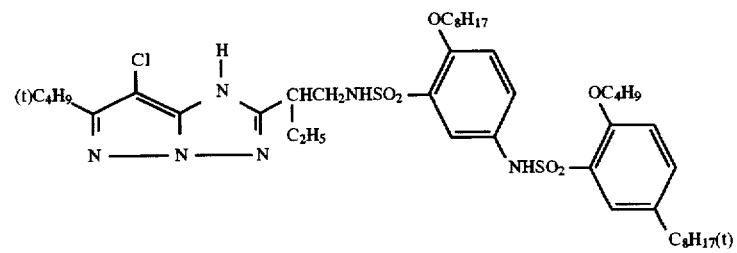
(M-41)
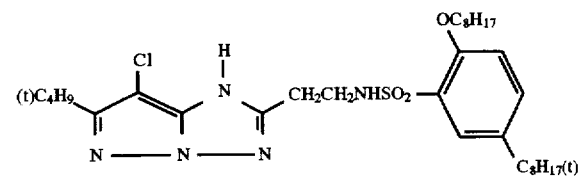
(M-42)
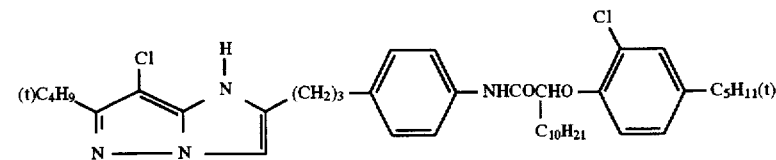
(M-43)
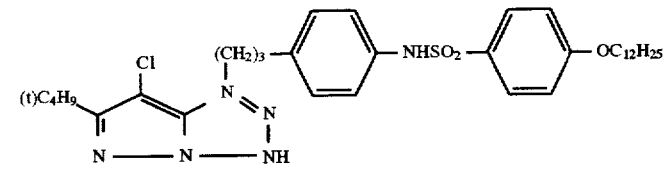
(M-44)
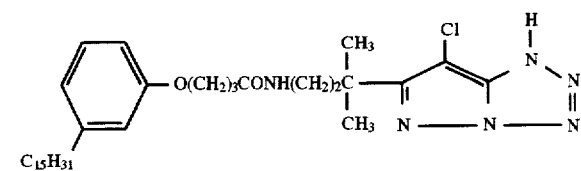

-continued
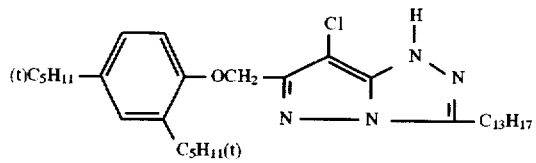
(M-45)
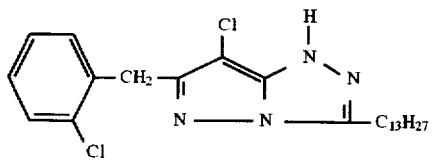
(M-46)
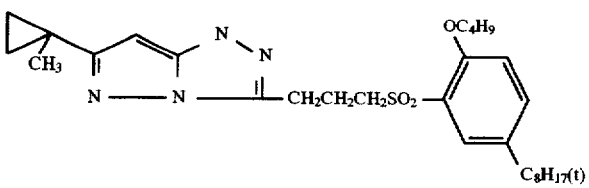
(M-47)
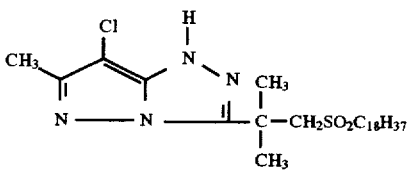
(M-48)
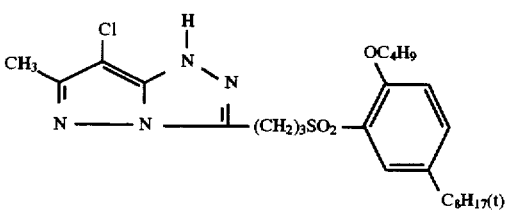
(M-49)
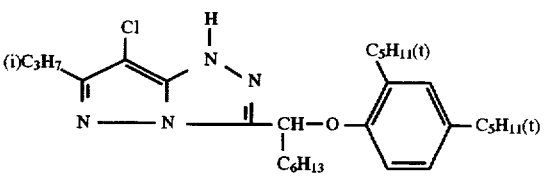
(M-50)
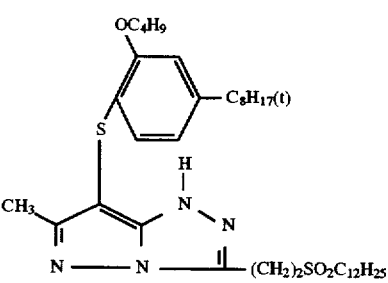
(M-51)
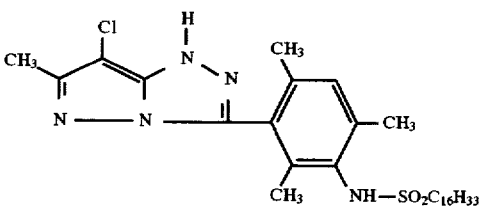
(M-52)

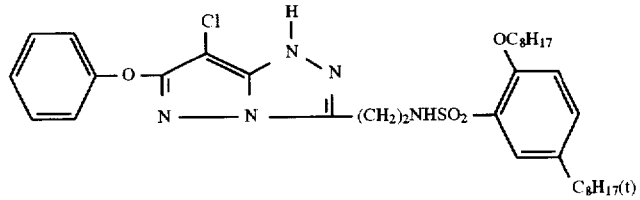
(M-53)
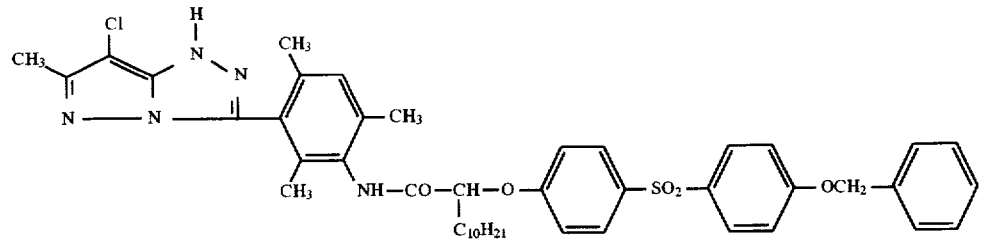
(M-54)
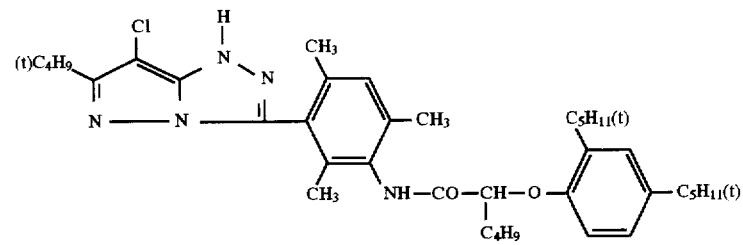
(M-55)
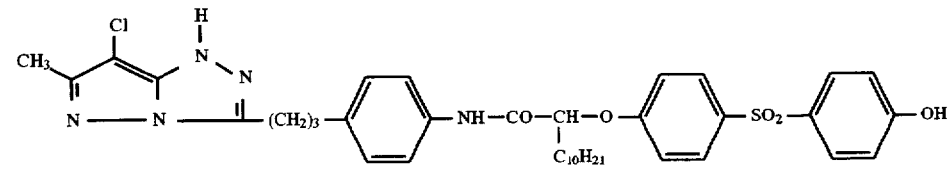
(M-56)
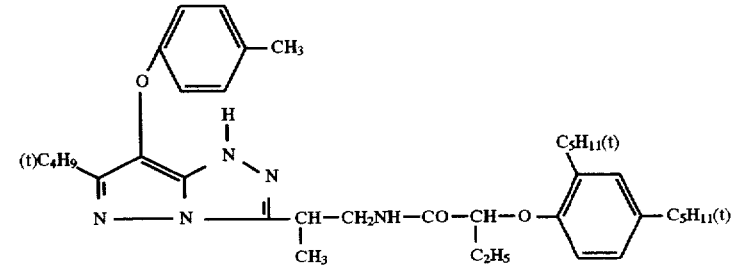
(M-57)
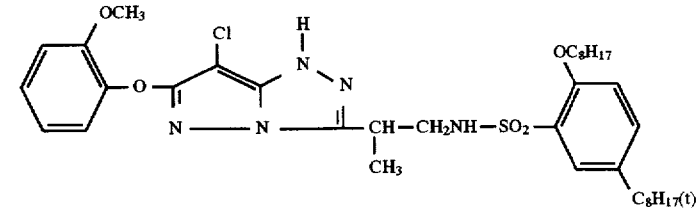
(M-58)
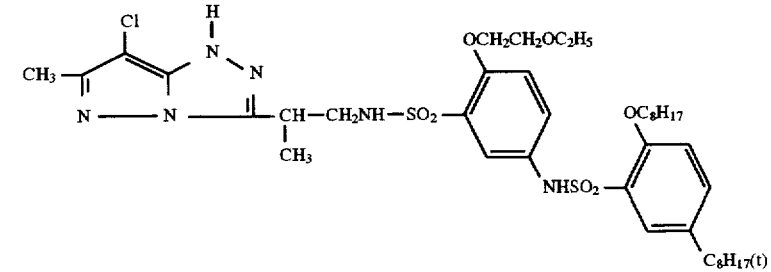
(M-59)

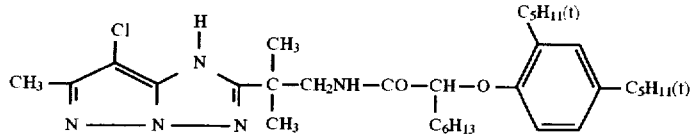 (M-60)

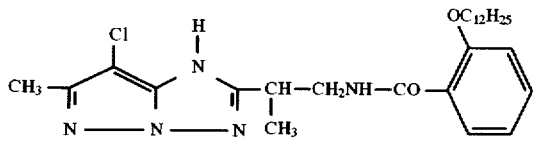 (M-61)

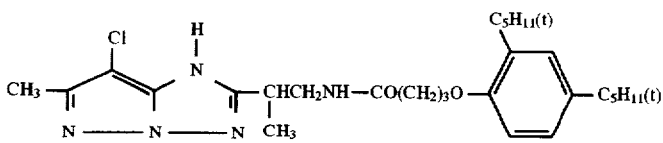 (M-62)

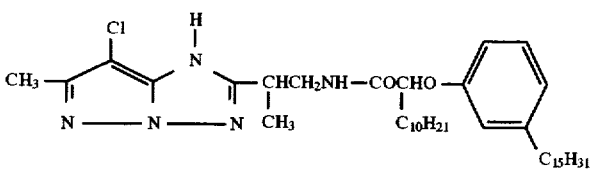 (M-63)

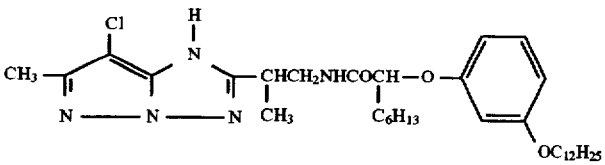 (M-64)

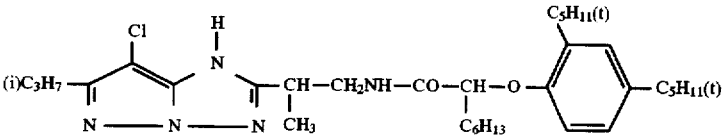 (M-65)

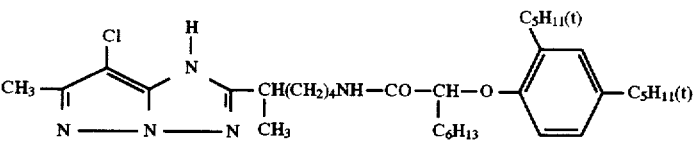 (M-66)

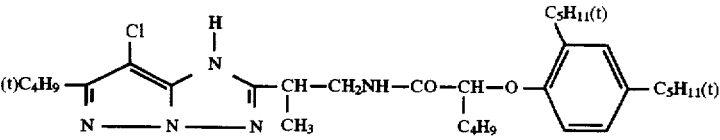 (M-67)

Cyan couplers may, for example, be derivatives of phenol, of 1-naphthol or of pyrazolo-quinazolone. Preferred structures are those of the formula E

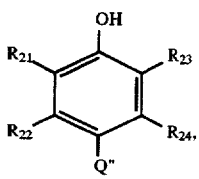 (E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl. $R_{22}$ is preferably an alkyl or amino group. $R_{23}$ is preferably an amino group and $R_{24}$ is preferably hydrogen. Q" is hydrogen or a leaving group which is eliminated during reaction with the oxidized developer. A detailed listing of cyan couplers is given in U.S. Pat. No. 4,456,681.

Examples of common cyan couplers are the following:

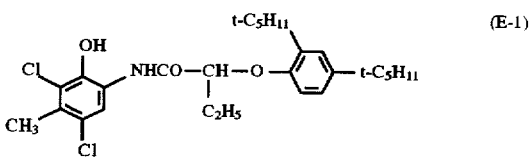 (E-1)

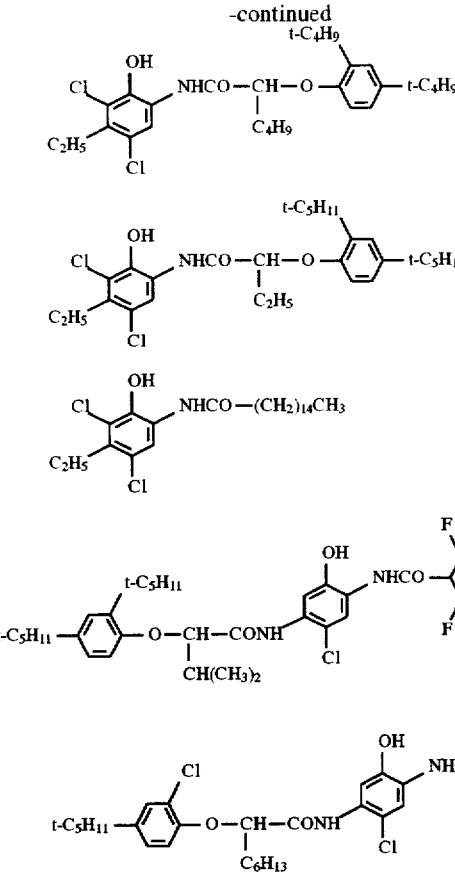

Further examples of cyan couplers are given in the following U.S. Pat. No. documents: 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183 and 4,923,791 and in EP-A-354,549 and EP-A-398,664.

In the red-sensitive silver-halide emulsion layer of the novel material, cyan couplers of the formula

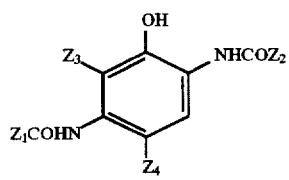

and/or of the formula

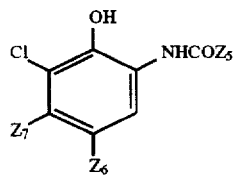

are preferably employed, in which $Z_1$ is alkyl, aryl, $Z_2$ is alkyl, cycloalkyl, aryl, a heterocyclic group or a ballast group, $Z_3$ is hydrogen or halogen, $Z_1$ and $Z_3$ together may form a ring, and $Z_4$ is hydrogen or a leaving group, and $Z_5$ is a ballast group, $Z_6$ is hydrogen or a leaving group and $Z_7$ is alkyl.

The colour developers usually used for colour-photographic recording materials are p-dialkylaminoanilines. Examples of these are 4-amino-N, N-diethylaniline, 3-methyl-4-amino-N,N-diethylaniline, 4-amino-N-ethyl-N-α-hydroxyethylaniline,
3-methyl-4-amino-N-ethyl-N-α-hydroxyethylaniline,
3-methyl-4-amino-N-ethyl-N-α-hydroxyethylaniline,
3 - m e t h y l - 4 - a m i n o - N - e t h y l - N - α - methanesulfonamidoethylaniline,
3-methyl-4-amino-N-ethyl-N-α-methoxyethyl-aniline,
3-α-methanesulfonamidoethyl-4-amino-N,N-diethylaniline,
3-methoxy-4-amino-N-ethyl-N-α-hydroxyethylaniline,
3-methoxy-4-amino-N-ethyl-N-α-methoxyethylaniline,
3-acetamido-4-amino-N,N-diethylaniline, 4-amino-N,N-dimethylaniline,
N-ethyl-N-α-|α'-(α"-methoxyethoxy)ethoxy|ethyl-3-methyl-4-aminoaniline,
N-ethyl-N-α-(α'-methoxyethoxy)ethyl-3-methyl-4-aminoaniline, and also the salts of such compounds, for example sulfates, hydrochlorides or toluenesulfonates.

The compounds of the formula I which can be used in the context of this invention can be incorporated into the colour-photographic recording material, on their own or together with the colour coupler and with or without further additives, by predissolving them in high-boiling organic solvents. Preference is given to the use of solvents which boil at higher than 160° C.

Typical examples of these solvents are the esters of phthalic acid, phosphoric acid, citric acid, benzoic acid or of fatty acids, and also alkylamides and phenols.

A low-boiling solvent is usually used in addition in order to simplify incorporation of the additives into the colour-photographic recording material. Examples of such solvents are esters, for example ethyl acetate, alcohols, for example butanol, ketones, for example methyl isobutyl ketone, chlorinated hydrocarbons, such as methylene chloride, and amides, such as dimethylformamide. Where the additives themselves are liquid, they can also be incorporated into the photographic material without the assistance of solvents.

The novel compounds of the formula I may if desired be dispersed in the gelatine layer without oil; Research Disclosure 88/296017 and 89/303070.

Further details regarding high-boiling solvents which can be used are given in the following publications:
phosphates: GB-A-791,219, BE-A-755,248, JP-A-76/76739, 78/27449, 78/218,252, 78/97573, 79/148,133, 82/216,177, 82/93323 and 83/216,177 and EP-A-265, 296.
phthalates: GB-A-791,219, JP-A-77/98050, 82/93322, 82/216,176, 82/218,251, 83/24321, 83/45699, 84/79888.
amides: GB-A-791,129, JP-A-76/105,043, 77/13600, 77/61089, 84/189,556, 87/239,149, U.S. Pat. No. 928, 741, EP-A-270,341, WO 88/00723.
phenols: GB-A-820,329, FR-A-1,220,657, JP-A-69/69946, 70/3818, 75/123,026, 75/82078, 78/17914, 78/21166, 82/212,114 and 83/45699.
Other oxygen-containing compounds: U.S. Pat. Nos.3, 748,141, 3,779,765, JP-A-73/75126, 74/101,114, 74/10115, 75/101,625, 76/76740, 77/61089, EP-A-304,81 0 and BE-A-826,039.
Other compounds: JP-A-72/115,369, 72/130,258, 73/127, 521, 73/76592, 77/13193, 77/36294, 79/95233, 91/2,748, 83/105,147 and Research Disclosure 82/21918.

The amount of high-boiling solvent is, for example, in the range from 50 mg to 2 g per $m^2$ of base, preferably from 200 mg to 1 g per $m^2$.

The photographic layers may, furthermore, contain colour cast inhibitors. These prevent colour casts being formed due, for example, to reaction of the coupler with unintentionally oxidized developer or with by-products of the colour-formation process. Colour cast inhibitors of this kind are usually hydroquinine derivatives, but may also be derivatives of aminophenols, of gallic acid or of ascorbic acid. Typical examples of these inhibitors are given in the following publications: U.S. Pat. Nos. 2,360,290, 2,336,327, 2,403,721, 2,418,613, 2,675,314, 2,701,197, 2,704,713, 2,728,659, 2,732,300, 2,735,365; EP-A-124,877, EP-A-277, 589, EP-A-338,785; JP-A-75/92988, 75/92989, 75/93928, 75/110,337,84/5,247 and 77/146,235.

The photographic layers may also contain DIR couplers (DIR denotes Development Inhibition Release) which form colourless compounds with the oxidized developer. They are added to improve the sharpness and grain of the colour images.

The photographic layers in the novel material may also include further UV absorbers. These screen out the UV light and therefore protect the dyes, the couplers or other components against photodegradation. Examples of such UV absorbers are benzotriazoles, 2-hydroxybenzophenones, salicylic esters, acrylonitrile derivatives or thiazolines. UV absorbers of this type are described in more detail in the following publications: U.S. Pat. Nos. 3,314,794, 3,352,681, 3,705,805, 3,707,375, 4,045,229, 3,700,455, 3,533,794, 3,698,907, 3,705,805, 3,738,837, 3,762,272, 4,163,671, 4,195,999, 4,309,500, 4,431,726, 4,443,543, 4,576,908, 4,749,643, GB-A-1,564,089, EP-A-190,003 and JP-A-71/2784, 81/111,826, 81/27,146, 88/53,543 and 88/55,542.

Preferred UV absorbers are benzotriazoles, especially the 2-(2-hydroxyphenyl)benzotriazoles (HBT) of the formula

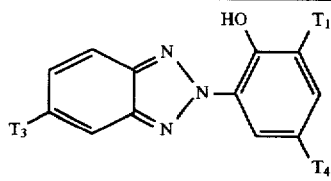

in which $T_1$, $T_2$ and $T_3$ independently of one another are hydrogen, halogen, alkyl, alkyl substituted by a carboxylic ester group, alkoxy, aryloxy, hydroxyl or acyloxy, and $T_4$ is hydrogen, alkoxy, aryloxy or acyloxy.

Particularly preferred such HBT compounds are those which are liquid at room temperature.

Examples of the preferred HBT compounds are:

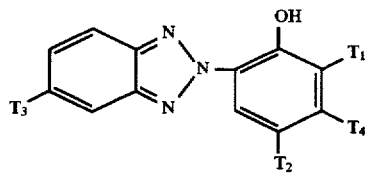

| HBT No. | $T_1$ | $T_4$ | $T_3$ |
|---|---|---|---|
| HBT-1 | H | $CH_3$ | H |
| HBT-2 | H | $C(CH_3)_3$ | H |
| HBT-3 | $C(CH_3)_3$ | $CH_3$ | Cl |
| HBT-4 | $C(CH_3)_3$ | $C(CH_3)_3$ | Cl |
| HBT-5 | $C(CH_3)_3C_2H_5$ | $C(CH_3)_3C_2H_5$ | H |
| HBT-6 | $CH(CH_3)C_2H_5$ | $C(CH_3)_3$ | H |

-continued

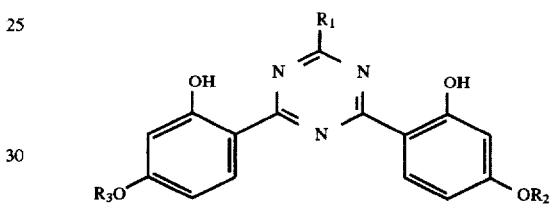

| HBT No. | $T_1$ | $T_4$ | $T_3$ |
|---|---|---|---|
| HBT-7 | $C(CH_3)_2$—⟨phenyl⟩ | $C(CH_3)_2$—⟨phenyl⟩ | H |
| HBT-8 | $C(CH_3)_3$ | $CH_2CH_2COOC_8H_{17}$ (isomers) | Cl |
| HBT-9 | $C(CH_3)_3$ | $CH_2CH_2COOC_8H_{17}$ (isomers) | H |
| HBT-10 | $C_{12}H_{25}$ (isomers)* | $CH_3$ | H |

*principal product

Other preferred UV absorbers are 2-hydroxyphenyl-1,3,5-triazines of the formula

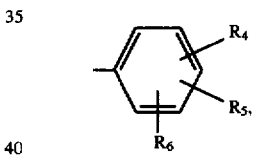

in which $R_1$ is a group of the formula

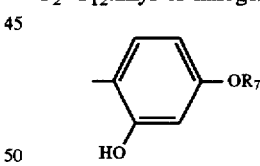

where $R_4$, $R_5$ and $R_6$ independently of one another are hydrogen, $C_2-C_{12}$alkyl or halogen, —⟨phenyl⟩—$OR_7$
         |
         HO and
or $R_1$ is a group of the formula $R_2$, $R_3$ and $R_7$ independently of one another are monovalent organic radicals. Preferably, $R_2$, $R_3$ and $R_7$ independently of one another are a radical $CH_2CH(OR_8)CH_2OR_9$, in which $R_8$ is hydrogen or acetyl and $R_9$ is $C_1-C_{18}$alkyl.

The photographic layers may also contain phenolic compounds which act as light stabilizers for the colour image and as colour cast inhibitors. They may be present in a photosensitive layer (colour layer) or in an interlayer, alone or together with other additives. Such compounds are described in greater detail, for example, in the following publications: U.S. Pat. Nos. 3,700,455, 3,591,381, 3,573, 052, 4,030,931, 4,174,220, 4,178,184, 4,228,235, 4,279,990, 4,346,165, 4,366,226, 4,447,523, 4,528,264, 4,581,326, 4,562,146, 4,559,297, GB-A-1,309,277, 1,547,302, 2,023, 862, 2,135,788, 2,139,370, 2,156,091; DE-A-2,301,060, 2,347,708, 2,526,468, 2,621,203, 3,323,448; DD-A-200, 691, 214,468; EP-A-106,799, 113,124, 125,522, 159,912, 161,577, 164,030, 167,762, 176,845, 246,766, 320,776; JP-A-74/134,326, 76/127,730, 76/30462, 77/3822, 77/154, 632, 78/10842, 79/48535, 79/70830, 79/73032, 79/147,038, 79/154,325, 79/155,836, 82/142,638, 83/224,353, 84/5246, 84/72443, 84/87456, 84/192,246, 84/192,247, 84/204,039, 84/204,040, 84/212,837, 84/220,733, 84/222,836, 84/228, 249, 86/2540, 86/8843, 86/18835, 86/18836, 87/11456, 87/42245, 87/62157, 86/6652, 89/137,258 and in Research Disclosure 79/17804.

The photographic layers may also contain certain phosphorus(III) compounds, especially phosphites and phosphonites. These act as light stabilizers for the colour images and as dark-storage stabilizers for magenta couplers. They are preferably added to the high-boiling solvents together with the coupler. Phosphorus(III) compounds of this type are described in greater detail, for example, in the following publications: U.S. Pat. No. 4,407,935, U.S. Pat. No. 4,436,81 1, U.S. Pat. No. 4,956,406, EP-A-1 81,289, JP-A-73/32 728, JP-A-76/17 420 and JP-A-55/66741.

The photographic layers may also contain organometallic complexes which are light stabilizers for the colour images, especially for the magenta dyes. Such compounds and combinations thereof with other additives are described in greater detail, for example, in the following publications: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A-81/167,138, 81/168,652, 82/30834, 82/161,744; EP-A-1 37,271, 161,577,185,506; DE-A-2,853, 865.

The photographic layers may also contain hydroquinone compounds. These act as light stabilizers for the colour couplers and for the colour images and as scavengers of oxidized developer in interlayers. They are use d in particular in the magenta layer. Hydroquinone compounds of this type and combinations thereof with other additives are described in greater detail, for example, in the following publications: U.S. Pat. Nos. 2,360,290, 2,336,327,2,403, 721,2,418,613,2,675,314,2,701,197,2,710,801,2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, 4,559,297, FR-A-885,982; GB-A-891,158, 1,156,167, 1,363,921, 2,022,274, 2,066,975, 2,071,348, 2,081,463,2, 117,526, 2,156,091; DE-A-2,408,168, 2,726,283, 2,639, 930, 2,901,520, 3,308,766, 3,320,483, 3,323,699; DD-A-216,476, 214,468, 214,469, EP-A-84290, 110,214, 115,305, 124,915, 124,877, 144,288, 147,747, 178,165, 161,577; JP-A-75/33733, 75/21249, 77/128,130, 77/146,234, 79/70036, 79/133,131, 81/83742, 81/87040, 81/109,345, 83/134,628, 82/22237, 82/112,749, 83/17431, 83/21249, 84/75249, 84/149,348, 84/182,785, 84/180,557, 84/189,342, 84/228,249, 84/101,650, 79/24019, 79/25823, 86/48856, 86/48857, 86/27539, 86/6652, 86/72040, 87/11455, 87/62157, and in Research Disclosure 79117901, 79/17905, 79/18813, 83/22827 and 84/24014.

The photographic layers may also include derivatives of hydroquinone ethers. These compounds act as light stabilizers and are particularly suitable for stabilizing magenta dyes. Such compounds and combinations thereof with other additives are described in more detail, for example, in the following publications: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297; GB-A 1,347,556, 1,366,441, 1,547, 392, 1,557,237, 2,135,788; DE-A 3,214,567; DD-214,469, EP-A 161,577, 167,762, 164,130, 176,845; JP-A 76/123, 642, 77/35633, 77/147,433, 78/126, 78/10430, 78/53321, 79/24019, 79/25823, 79/48537, 79/44521, 79/56833, 79/70036, 79/70830, 79/73032, 79/95233, 79/145,530, 80/21004, 80/50244, 80/52057, 80/70840, 80/139,383, 81/30125, 81/151,936, 82/34552, 82/68833, 82/ 204,306 82/204,037, 83/134,634, 83/207,039, 84/60434, 84/101,650, 84/87450, 84/149,348, 84/182,785, 86/72040, 87/11455, 87/62157, 87/63149, 86/2151, 86/6652, 86/48855, 89/309, 058 and in Research Disclosure 78/17051.

Examples of suitable such stabilizers for the magenta couplers are:

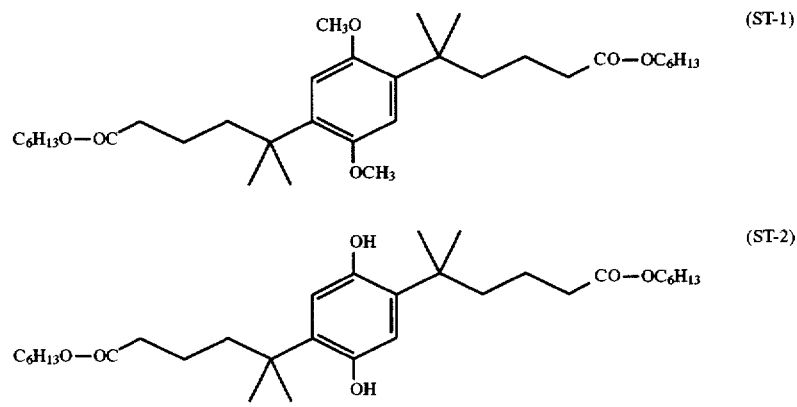

-continued

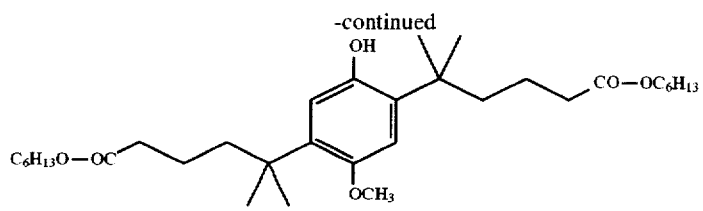 (ST-3)

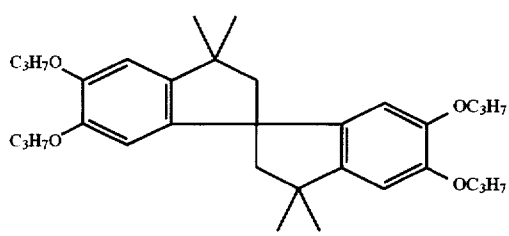 (ST-4)

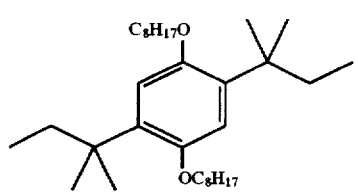 (ST-5)

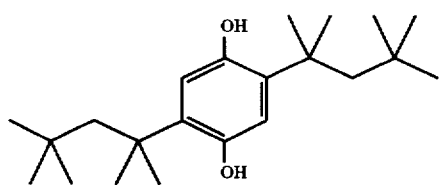 (ST-6)

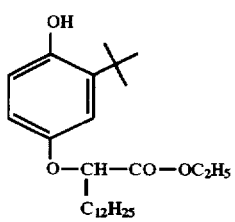 (ST-7)

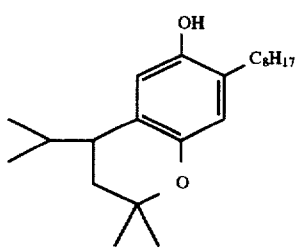 (ST-8)

Examples of further costabilizers are those of the formulae P, SA, SB, HQ and RE below.

Compounds of the formula P

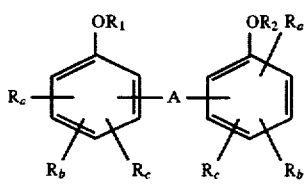

in which $R_1$ and $R_2$ independently of one another are hydrogen, acyl or alkyl;

$R_a$, $R_b$ and $R_c$ independently of one another are H, alkyl, cycloalkyl, aryl, halogen, alkoxy, aryloxy, acyloxy, alkylthio, arylthio, acyl, sulfonyl, sulfamoyl, acylamino, sulfonylamino or nitro;

A is a bond, $S(\!=\!O)_m$ , alkylene or —$NR_d$—;

$R_d$ is alkyl or acyl; and m is 0, 1 or 2.

Examples of compounds of the formula P:
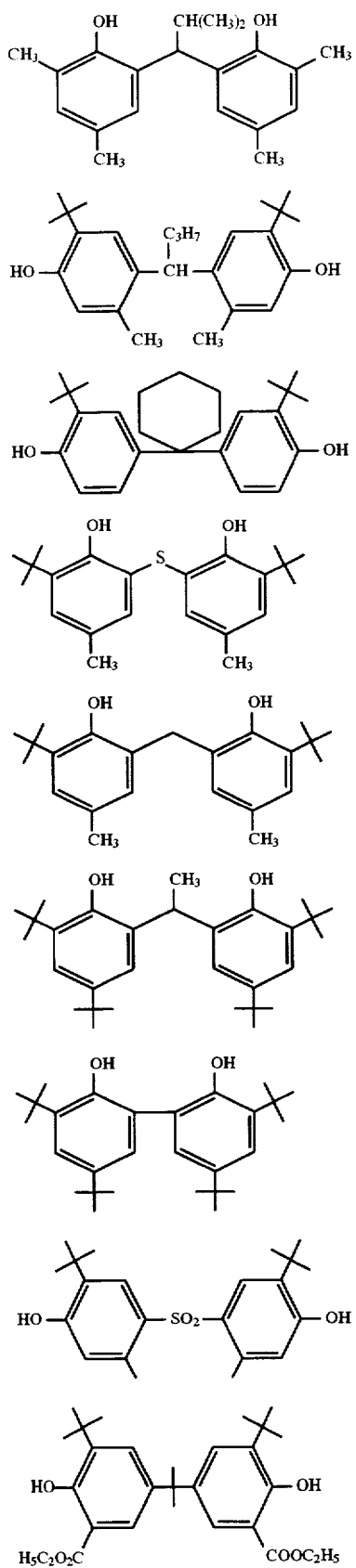
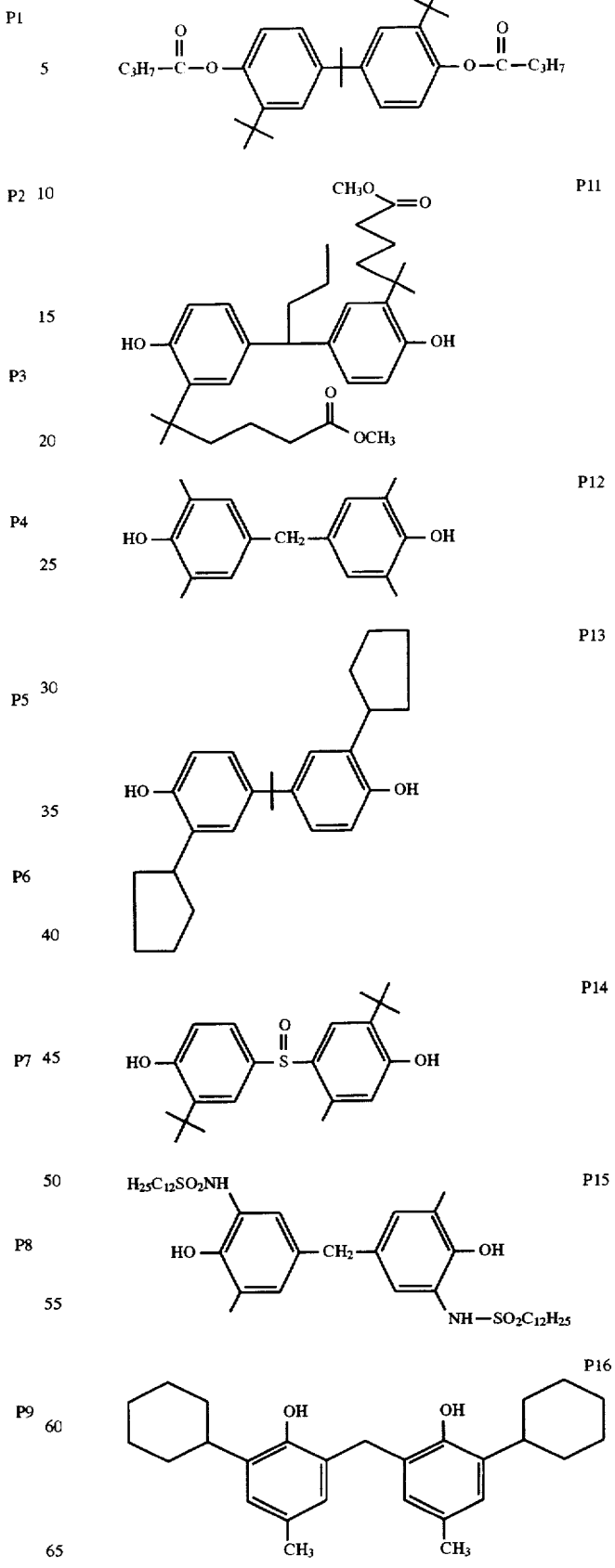

-continued
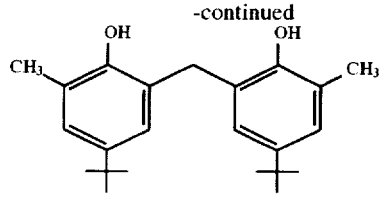 P17
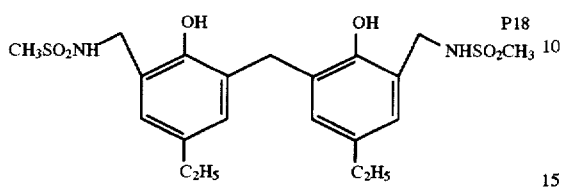 P18
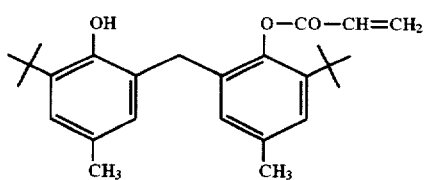 P19
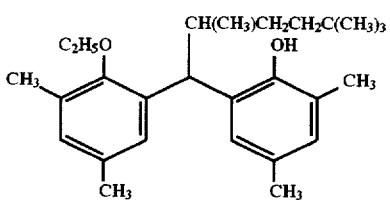 P20
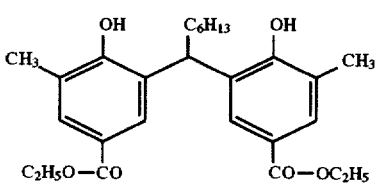 P21
-continued
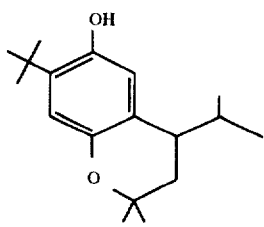 P22
Compounds of the formula SA
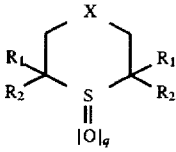
in which
R₁ is hydrogen;
R₂ is phenyl or
R₁ and R₂ are methyl;
q is 0, 1 or 2; and
X is a divalent radical which supplements the ring of the formula SA to make a tetra-hydrothiopyran ring.
For examples of compounds of the formula SA see U.S. Pat. No. 4 993 271, and
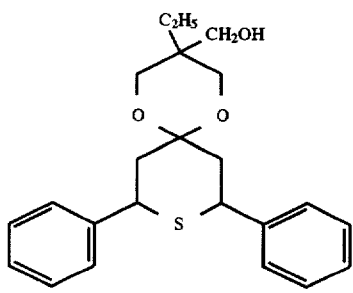 SA 1
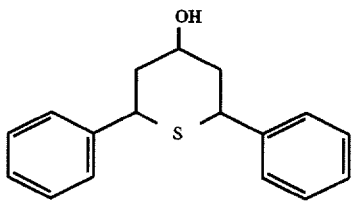 SA 2
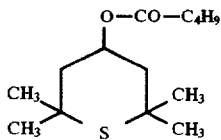 SA 3

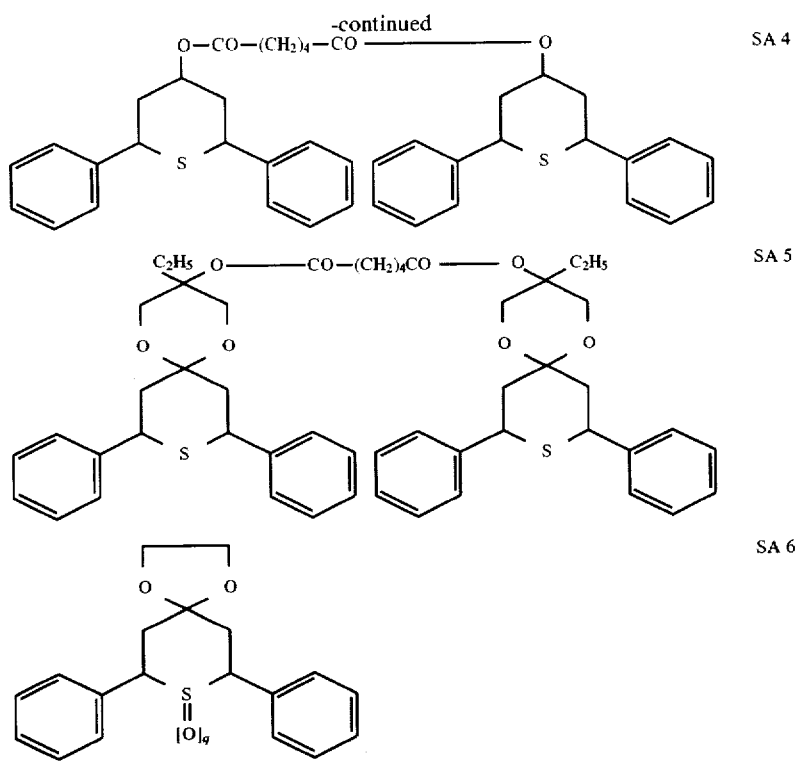

SA 4

SA 5

SA 6

Compounds of the formula SB $$R_3-S-(C_pH_{2p})-Z-R_4$$

in which $R_3$ is alkyl, aryl or a group $(C_pH_{2p})-Z-R_4$;
p is 1-12;
Z is —CO—O— or —O—CO—;
$R_4$ is a mono-, di-, tri- or tetravalent group.

Examples of compounds of the formula SB:

| | |
|---|---|
| $C_{12}H_{25}-S-CH_2CH_2CO-O-C_4H_9$ | SB1 |
| $S(CH_2CH_2CO-OC_4H_9)_2$ | SB2 |
| 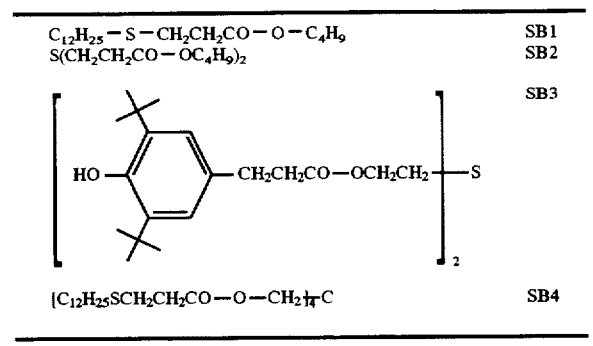 | SB3 |
| $[C_{12}H_{25}SCH_2CH_2CO-O-CH_2]_4C$ | SB4 |

Compounds of the formula HQ

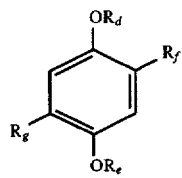

in which $R_e$ and $R_d$ independently of one another are alkyl or cycloalkyl; and $R_f$ and $R_g$ independently of one another are as defined for $R_a$, $R_b$, $R_c$.

Examples of compounds of the formula HQ:

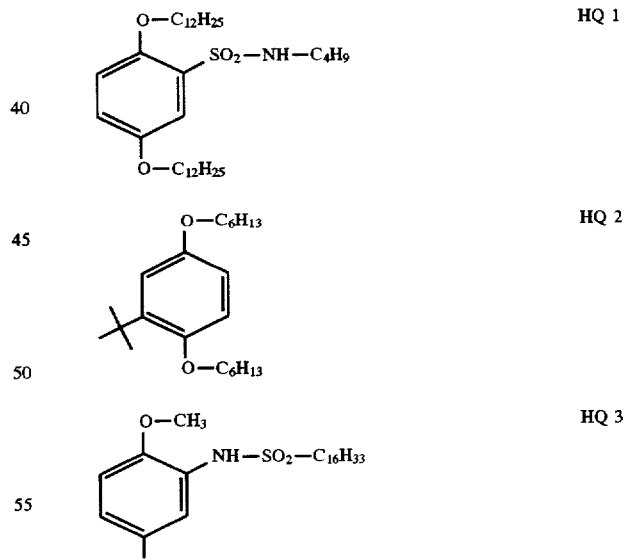

-continued

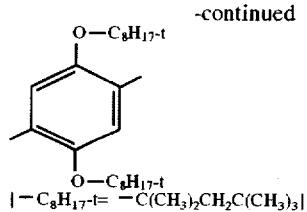
[—C₈H₁₇-t= —C(CH₃)₂CH₂C(CH₃)₃]

HQ 5

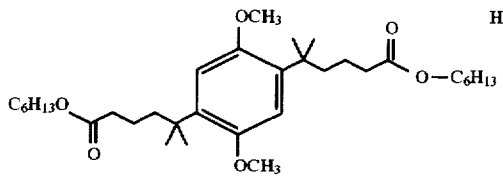

HQ 6

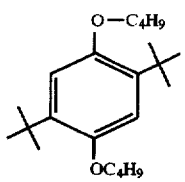

HQ 7

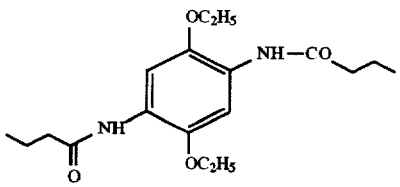

HQ 8

Compounds of the formula RE

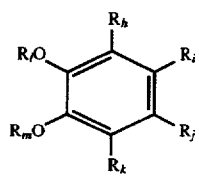

in which

R$_l$ and R$_m$ independently of one another are H, acyl or alkyl; or R$_l$ and R$_m$ together are attached to a P—O-aryl radical; and R$_h$, R$_i$, R$_j$ and R$_k$ independently of one another are as defined for R$_a$, R$_b$, R$_c$, with the proviso that at least one of the radicals R$_i$ and R$_j$ is not alkyl.

Examples of compounds of the formula RE:

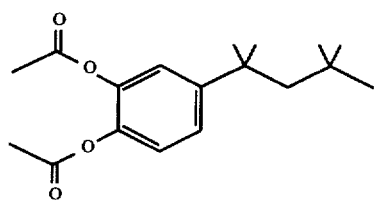

RE 1

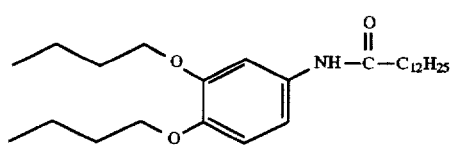

RE 2

-continued

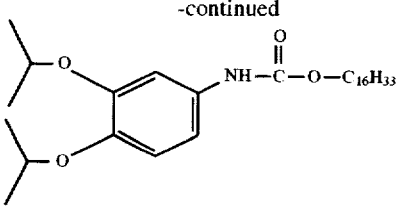

RE 3

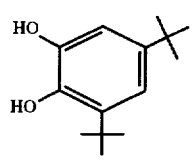

RE 4

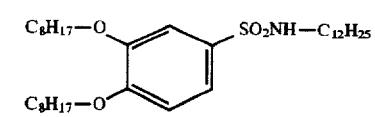

RE 5

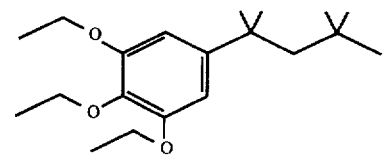

RE 6

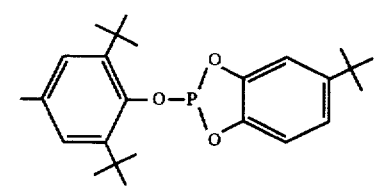

RE 7

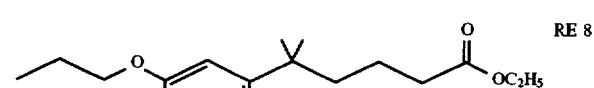

RE 8

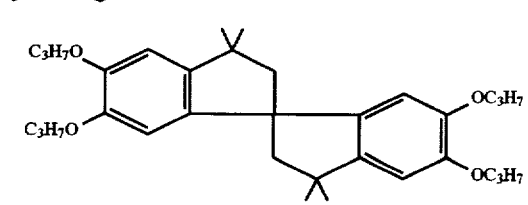

RE 9

As silver halide emulsions it is possible to use customary silver chloride, silver bromide or silver iodide emulsions or mixtures thereof, such as silver chlorobromide and silver chloro-iodide emulsions, in which the silver halides may have all known crystal forms. The use of silver chloride emulsions is accorded particular importance in the novel material. The preparation of such emulsions and their sensitization are described in RESEARCH DISCLOSURE, November 1989, No. 307,105. This publication also mentions a range of binders for these emulsions, which may also be employed in the novel materials. The same applies to the bases mentioned in the publication.

The silver halide emulsion which can be used to implement this invention can be sensitized for all desired wavelengths, with the aid of sensitizing pigments. Pigments which can be used for this purpose are cyanine pigments, merocyanine pigments, holopolar pigments, hemicyanine pigments, styryl pigments or hemioxonol pigments.

The photosensitive material may include water-soluble dyes in order, for example, to improve the clarity, which they do by preventing radiation damage. Dyes which can be used for this purpose are oxonol dyes, hemioxonol dyes, styryl dyes, merocyanine dyes, cyanine dyes, anthraquinone dyes and azo dyes.

Along with the novel material it is also possible to use further materials, as described, for example, in JP-A-87/215 272, 92/9 035, 92/21 840 and EP-A-429 240.

Finally, the invention also relates to a method of stabilizing magenta couplers and magenta dyes in colour-photographic recording materials using the novel O-phenol-substituted aminophenol derivatives of the formula I.

For this purpose, these compounds are dissolved in an organic solvent or solvent mixture and the solution is emulsified in a gelatine solution, which is then added to the photographic gelatine layer in the course of its preparation. The solvents used preferably constitute a mixture of a low-boiling and a high-boiling solvent, and the low-boiling solvent is removed in the course of emulsification.

The operation of dispersing the stabilizer solution in the gelatine solution can be carried out, for example, in a colloid mill or in a homogenizer, or with the aid of ultrasound. In the course of this operation it is also possible to add surfactants (emulsifiers). Fine dispersion is a prerequisite for the homogeneous distribution of the stabilizers in the photographic layer.

The compounds of the formula I stabilize both the colour couplers and the photo dyes, which are formed following exposure and development, against the effects of light. They prevent or delay bleaching or alteration in colour of the photo dyes under the effect of light. They do not react with the customary dye couplers, and have no adverse effects on the photographic process of colour formation.

The examples which follow illustrate the invention in more detail without limiting it. In the examples, as in the rest of the description and in the claims, parts and percentages are by weight unless stated otherwise. tBu denotes tert-butyl.

EXAMPLE 1

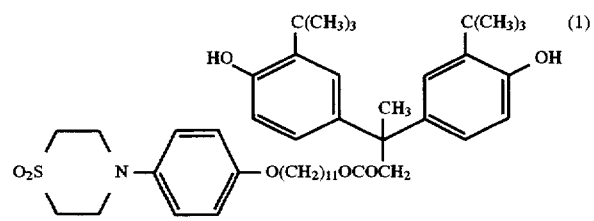
(1)

A mixture of 1.0 g (2.5 mmol) of the compound of the formula

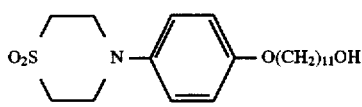

and 1.0 g (2.5 mmol) of the compound of the formula

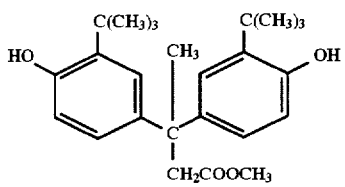

together with 0.1 g of dibutyltin oxide in 5 ml of toluene are heated at 150° C. for 20 hours under a nitrogen atmosphere. The crude product is chromatographed over silica gel (hexane/ethyl acetate 1:1) to give 0.7 g of the above compound (1) as a resin having the following analytical values:

Elemental analysis: $C_{45}H_{65}NO_7S$: calculated: C 70.74% H 8.58% N 1.83%; found: C 69.94% H 8.55% N 1.58%; $^1$H-NMR (300 MHz, CDCl$_3$): 7.06 (d, 2H), 6.82–6.91 (m, 6H), 6.52 (d, 2H), 3.91 (t, 2H), 3.81 (t, 2H), 3.65–3.68 (m, 4H), 3.11–3.15 (m, 4H), 3.04 (s, 2H), 1.82 (s, 3H), 1.11–1.57 (m, 32H including 1 s for 9H at 1.33).

EXAMPLES 2 to 5

The following compounds are prepared by the method indicated in Example 1, using the corresponding esters and alcohols as starting materials:

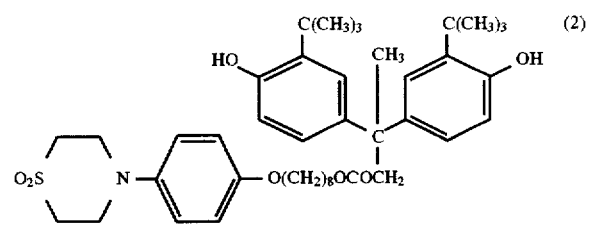
(2)

Yield: 65% of theory. Elemental analysis: $C_{42}H_{57}NO_7S$ (719.97); calculated: C 70.07% H 7.98% N 1.95%; found: C 69.29% H 8.10% N 1.75%;

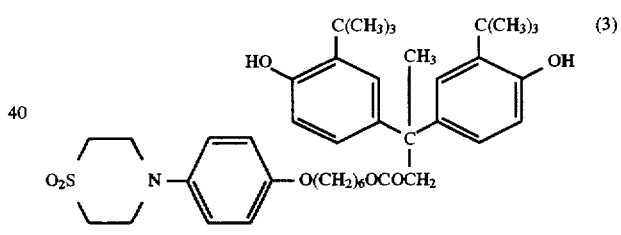
(3)

Yield: 46% of theory. Elemental analysis: $C_{40}H_{55}NO_7S$ (693.91); calculated: C 69.23% H 7.99% N 2.02%; found: C 68.94% H 8.11% N 1.64%;

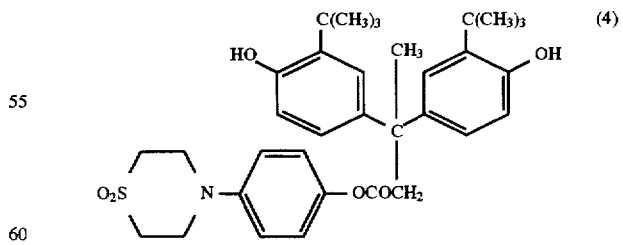
(4)

Yield: 32% of theory $^1$H-NMR (250 MHz): 7.11 (d,2H), 6.89 (dd,2H), 6.75 (d,2H), 6.55 (d,2H), 6.49 (d,2H), 4.78 (s,2H, OH), 3.70 (m,4H), 3.05 (m,4H), 2.15 (s,2H), 1.85 (s,3H), 1.29 (s,18H).

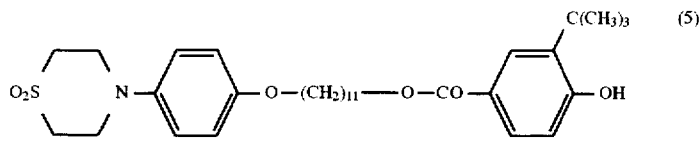
(5)

Yield: 98% of theory ¹H-NMR (250 MHz): 7.97 (d,1 H), 7.75 (dd,1H), 6.87 (d,2H) 6.81 (d,2H), 6.65 (dd,1H), 4.25 (t,2H), 3.89 (t,2H), 3.65 (m,4H), 3.13 (m,4H), 1.75 (m,2H) 1.39 (s,9H), 1.24 (m,16H).

6.87 (2d, 2×2H), 6.64 (dd,1H), 5.52 (bs,1H), 4.59 (t,2H), 4.24 (t,2H), 3.67 (m,4H) 1.38 (s,9H), 3.09 (m,4H) 1.38 (s,9H).

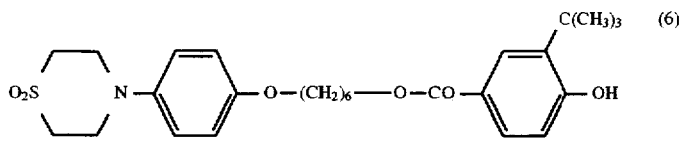
(6)

Yield: 39% of theory ¹H-NMR (250 MHz): 7.97 (d,1H), 7.75 (dd,1H), 6.88 (d,2H), 6.78 (d,2H), 6.64 (d,1H), 5.61 (s,1H,OH), 4.27 (t,2H), 3.90 (t,2H), 3.65 (m,4H), 3.11 (m,4H), 1.76 (m,4H), 1.50 (m,4H), 1.39 (s,9H).

EXAMPLE 7

To a solution of the alcohol (0.2 mol) of the formula

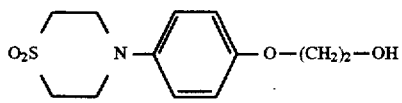

and triethylamine (0.25 mol) in 200 ml of toluene, a solution of the acid chloride (0.21 mol) of the formula

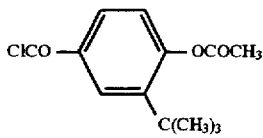

in toluene is slowly added dropwise at 60° C., and the mixture is stirred at 60° C. for 4 hours. After cooling, the reaction mixture is washed with water and dried over Na₂SO₄ and the solvent is evaporated. The residue is refluxed for 15 minutes with 250 ml of methanol containing 32 g of K₂CO₃. The reaction mixture is poured into 200 ml of water, subjected twice to extraction with ethyl acetate (200 ml each time), washed with water and concentrated by evaporation. The residue is chromatographed over silica gel using ethyl acetate/petroleum ether as eluent, to give the compound of the formula

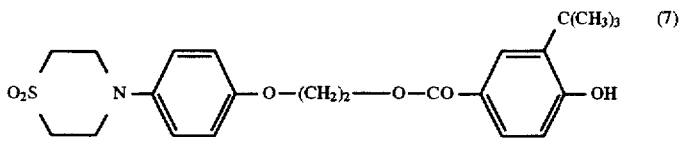
(7)

in a yield of 33% of theory.

Elemental analysis: C₂₃H₂₉NO₆S (447.55); calculated: C 61.73% H 6.53% N 3.13%; found C 61.85% H 6.43% N 2.76%; ¹H-NMR (300 MHz): 7.97 (d,1H), 7.72 (dd,1H),

EXAMPLE 8

A mixture of 1 mol of the compound of the formula

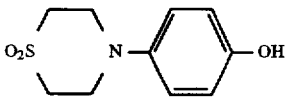

and 1.13 mol of ethylene carbonate of the formula

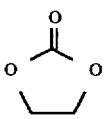

is heated at 165° C. for 3.5 hours under nitrogen, in the course of which CO₂ is given off and the compound of the formula

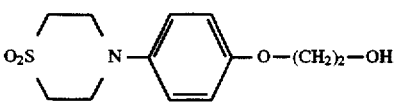

is formed. After cooling to 130° C., 1.2 l of toluene and then 1.13 mol of t-butyl acetoacetate (CH₃—CO—CH₃—CO—O—C(CH₃)₃) are added to the reaction mixture. The solution is refluxed for 2 hours, and t-butanol and toluene are slowly distilled off. The residue is freed from residual toluene under vacuum (80 mbar) and is recrystallized from ethyl acetate, to give 305 g (86% of theory) of the compound of the formula

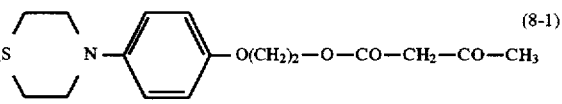
(8-1)

Elemental analysis $C_{16}H_{21}NO_6S$ (335.4); calculated: C 54.07% H 5.96% N 3.94%; found: C 54.05% H 5.97% N 3.89%

HCl gas is passed slowly at 20° C., over the course of 5 hours, into a solution of 0.5 mol of the compound of formula 8-1 and 5 mol of 2-tert-butylphenol in 240 ml of toluene, which still contains 2 g of ethylmercaptan. The reaction mixture is left to stand overnight at room temperature and is then heated at 90° C. for 1 hour to remove the HCl. Excess tert-butylphenol is removed by distillation at 150° C./2.5 mbar. The residue is dissolved in 700 ml of ethyl acetate, 15 g of $POCl_3$ are added to the resulting solution, and the mixture is stirred for 5 minutes. Then 500 ml of water, containing 40 g of sodium dithionite, are added and thorough stirring is carried out. The organic phase is separated off and dried over $Na_2SO_4$.

Following evaporation of the solvent, a pale yellow residue is obtained which becomes solid after drying in vacuo. This gives 299 g (90% of theory) of the compound of the formula

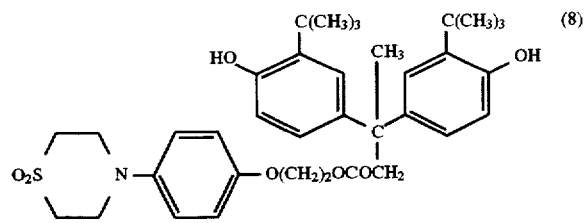
(8)

Elemental analysis: $C_{36}H_{47}NO_7S$ (637.84); calculated: C 67.79% H 7.43% N 2.20%; found: C 67.35% H 7.67% N 1.87%

The compound of the formula 8 is also obtained by the procedure of Example 1 using the corresponding ester and alcohol starting materials, in a yield of 75% of theory.

EXAMPLES 9-28

The following compounds are prepared by the method indicated in Example 1, using the corresponding esters and alcohols as starting material.

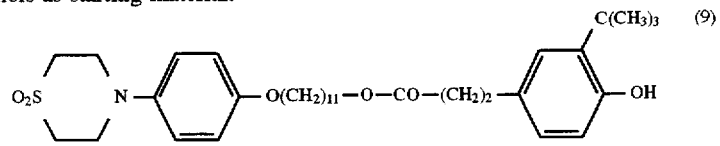
(9)

Yield: 75% $^1$H-NMR (250 MHz): 7.04 (d,1H), 6.85 (m,5H) 6.54 (d,1H), 5.02 (bs, 1H,OH), 4.09 (t,2H), 3.88 (t,2H), 3.64 (m,4H), 3.11 (m,4H) 2.85 (t,2H), 2.56 (t,2H), 1.73 (m,2H), 1.57 (m,2H), 1.36 (s,9H), 1.24 (m,14H).

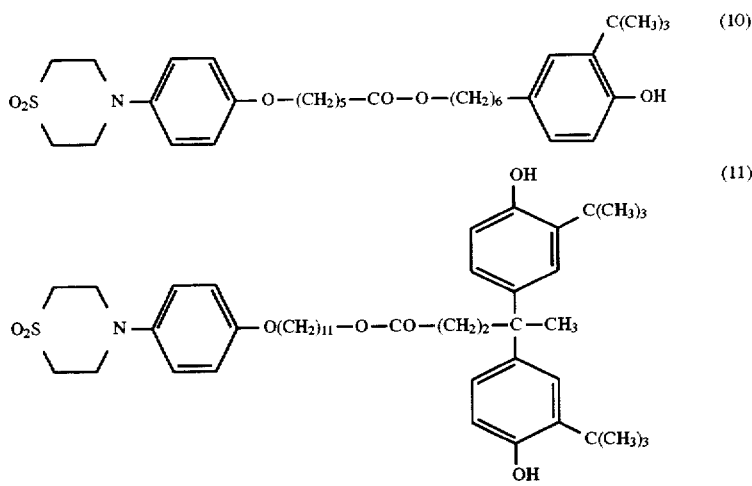

Yield: 64% of theory $^1$H-NMR (250 MHz): 7.02 (d,2H), 6.85 (m,6H), 6.52 (d,2H), 4.86 (bs, 2H, OH), 3.99 (t,2H), 3.89 (t,2H), 3.64 (m,4H), 3.11 (m,4H), 2.35 (m,2H), 2.10 (m,2H), 1.53 (s,3H and m,2H), 1.31 (s,9H), 1.24 (m,14H).

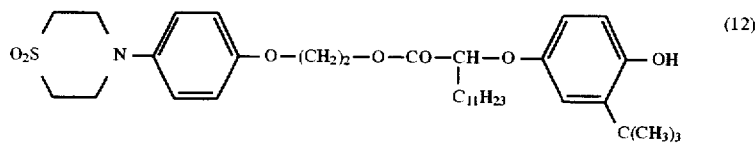
(12)
Yield: 68% of theory $^1$H-NMR (250 MHz): 6.89–6.78 (m, 5H), 6.53–6.45 (m,2H), 5.08 (s,1H,OH), 4.55–4.46 (m,16H), 4.11 (m,2H), 3.68 (m,4H), 3.12 (m,4H), 1.94 (m,2H), 1.51 (m,2H), 1.35 (s,9H), 1.25 (m,16H), 0.87 (t,3H). 4.35 (m,2H), 4.11 (m,2H), 3.67 (m,4H), 3.12 (m,4H), 2.23 (t,2H), 1.86 (m,2H), 1.37–1.30 (m,2H and s,6H).
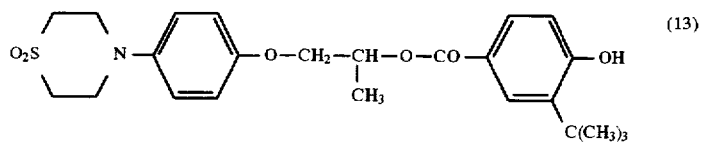
(13)
Yield: 21% of theory Melting point: 135° C.
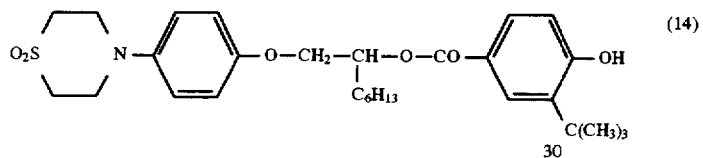
(14)
Yield: 47% of theory $^1$H-NMR (250 MHz): 7.97 (d,1H), 7.65 (dd,1H), 6.86 (d,2H), 6.83 (d,2H), 6.64 (d,1H), 5.76 (s,1H,OH), 5.34 (m,1H), 4.11 (m,2H), 3.65 (m,4H), 3.08 (m,4H), 1.76 (m,4H), 1.76 (m,2H), 1.38 (s,9H), 1.25 (m,8H), 0.84 (t,3H).
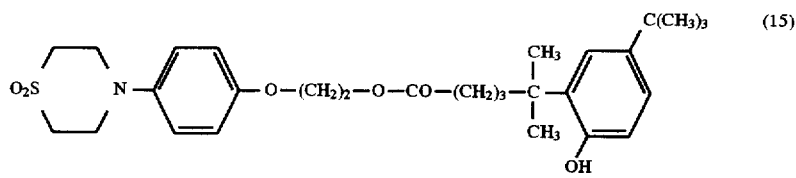
(15)
Yield: 91% of theory $^1$H-NMR (250 MHz): 7.19 (d,1H), 7.05 (dd,1H), 6.89 (d,2H), 6.87 (d,2H), 6.54 (d,1H), 4.80 (s,1H,OH), 4.36 (m,2H), 4.11 (m,2H), 3.67 (m,4H), 3.14 (m,4H), 2.20 (t,2H), 1.81 (m,2H), 1.35 (s,6H), 1.26 (s,9H).
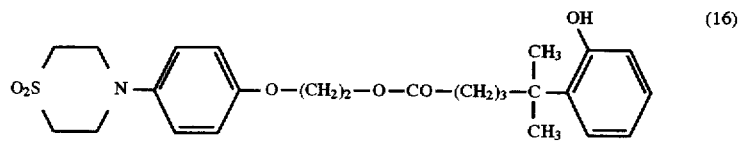
(16)
Yield: 29% of theory $^1$H-NMR (250 MHz): 7.18 (dd,1H), 7.04 (m,1H), 6.86 (m,5H), 6.59 (dd,1 H), 5.09 (bs,1H,OH),

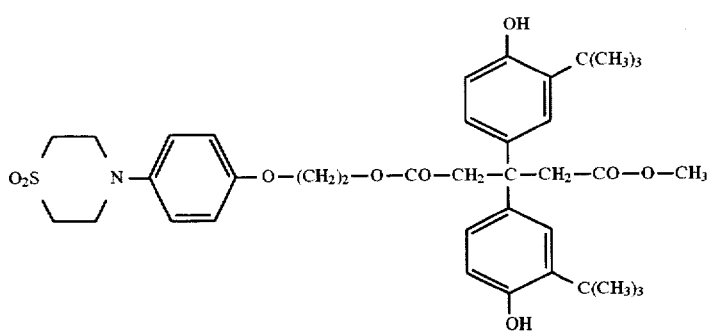
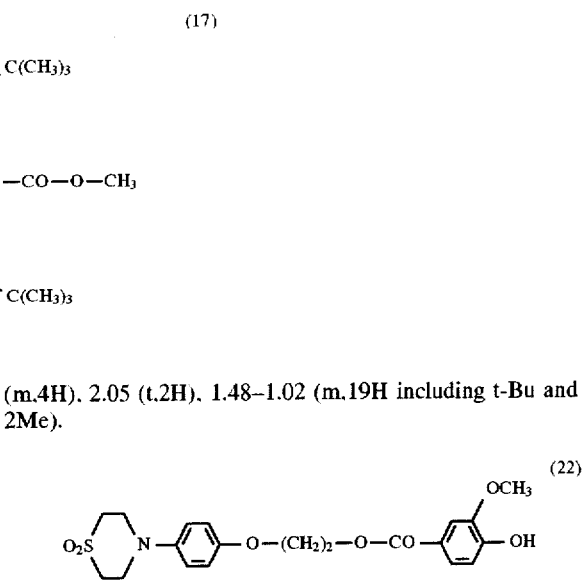

(17)

Yield: 77% of theory ¹H-NMR (250 MHz): 6.95 (m,2H), 6.84 (m,2H), 6.76 (m,4H), 6.43 (m,2H), 4.74 (s,2H,OH), (4.09 (m,2H), 3.76 (m,2H), 3.65 (m,4H), 3.47–3.37 (m,4H and s,3H), 3.11 (m,4H), 1.26 (m,18H including t-Bu).

(m,4H), 2.05 (t,2H), 1.48–1.02 (m,19H including t-Bu and 2Me).

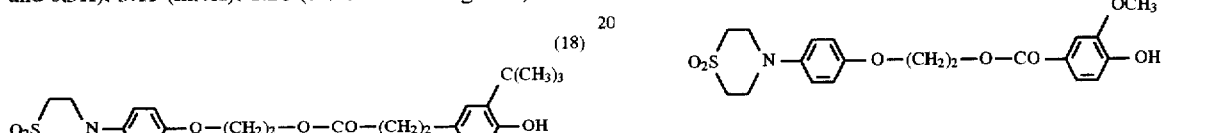

(18)

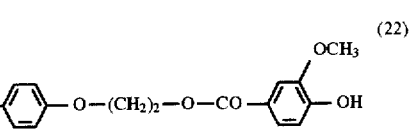

(22)

Yield: 50% of theory ¹H-NMR (300 MHz) 7.05 (d,1H), 6.86 (m,5H), 6.55 (dd,1H), 4.39 (m,2H), 4.08 (m,3H), 3.66 (m,4H), 3.11 (m,4H), 2.86 (t,2H), 2.61 (t,2H), 1.36 (s,9H).

Yield: 17% of theory ¹H-NMR (250 MHz) 7.61 (dd,1H), 7.53 (d,1H), 6.91 (m,5H), 6.02 (1H,OH), 4.60 (m,2H), 4.24 (m,2H), 3.91 (s,3H), 3.33 (m,4H), 3.12 (m,4H).

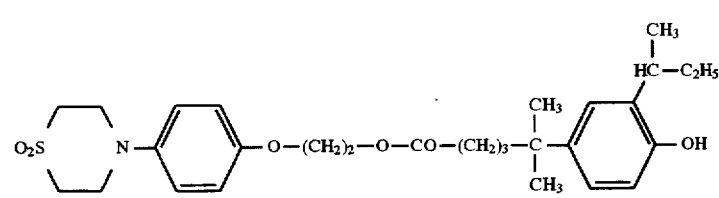

(19)

Yield: 27% of theory ¹H-NMR (250 MHz): 7.05–6.83 (m,6H), 6.62 (d,1H), 4.69 (s,1 H,OH), 4.33 (m,2H), 4.06 (m,2H), 3.65 (m,4H), 3.11 (m,4H), 2.89 (m,1H), 2.21 (m,2H), 1.57–1.11 (m,15H), 0.82 (t,3H).

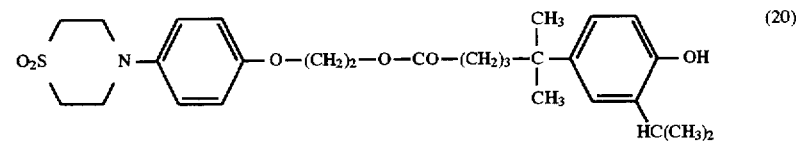

(20)

Yield: 40% of theory ¹H-NMR (250 MHz): 7.06 (d,1H), 6.93 (dd,1H), 6.84 (d,2H), 6.80 (d,2H), 6.59 (d,1H), 4.61 (s,1H,OH), 4.32 (m,2H), 4.06 (m,2H), 3.64 (m,4H), 3.11 (m,5H), 2.20 (m,2H), 1.53–1.20 (m,4H), 1.21 (s,6H), 1.19 (d,6H).

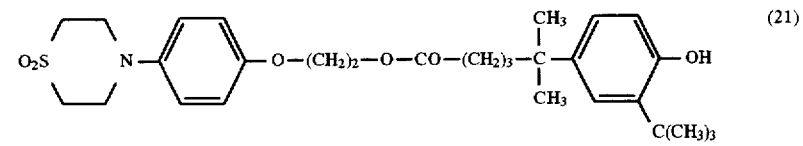

(21)

Yield: 47% of theory ¹H-NMR (250 MHz): 7.00 (d,1H), 6.79 (dd,1H), 6.75 (d,2H), 6.66 (d,2H), 6.37 (d,1H), 4.84 (s,1H,OH), 4.17 (m,2H), 3.93 (m,2H), 3.48 (m,4H), 2.96

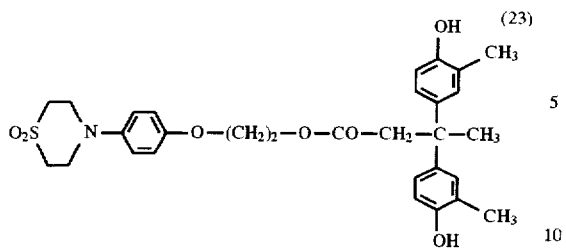
(23)
Yield: 41% of theory ¹H-NMR (250 MHz): 6.87–6.74 (m,8H), 6.56 (d,2H), 4.66 (s,2H,2OH), 4.16 (t,2H), 3.76 (t,2H), 3.67 (m,4H), 3.12 (m,4H), 2.12 (s,5H, 3H, 2H), 1.71 (s,6H).
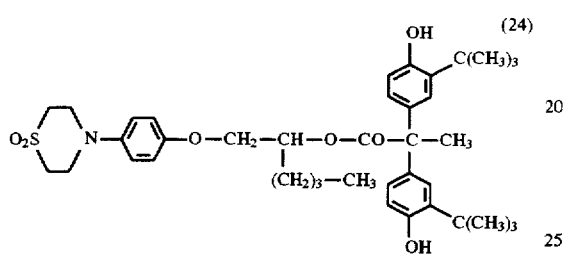
(24)
Yield: 28% of theory ¹H-NMR (300 MHz): 7.04 (d,2H), 6.85 (m,4H), 6.77 (d,2H), 6.52 (d,1H), 6.45 (d,1H), 4.94 (m,1H), 3.66 (m,4H), 3.11 (m,4H), 1.87–1.11 (m,30H including 2-t-Bu and CH₃ groups).
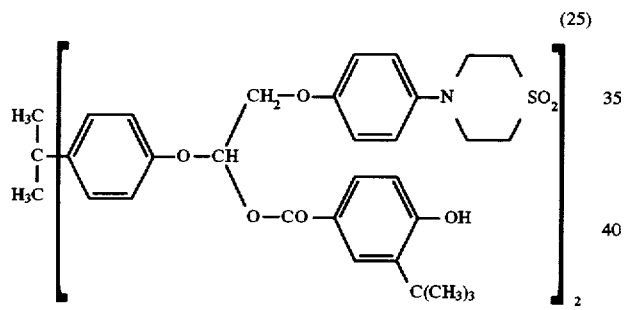
(25)
Yield: 29% of theory ¹H-NMR (250 MHz): 7.99 (d,2H), 7.66 (dd,2H), 7.10 (d,4H), 6.90–6.71 (m,12H), 6.63 (d,2H), 6.08 (bs, 2H,OH), 5.63 (t,2H), 4.33 (d,4H), 3.68 (m,8H), 3.10 (m,8H), 1.60 (s,6H), 1.39 (s,18H).
(26)
Yield: 53% of theory ¹H-NMR (300 MHz): 7.05 (d,2H), 6.89–6.76 (dd,1H and 2d,2×2H), 6.46 (d,2H), 4.78 (s,2H, OH), 4.16 (t,2H), 3.86 (m,4H), 3.78 (t,2H), 3.08 (m,4H), 1.62 (s,3H), 1.32 (s,18H).
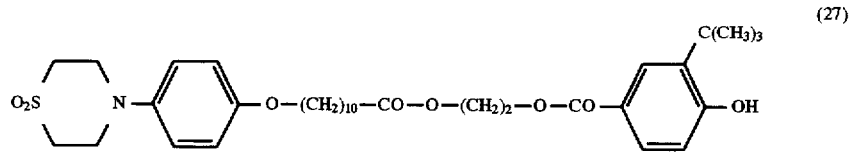
(27)
Yield: 23% of theory ¹H-NMR (250 MHz): 7.96 (d,1H), 7.76 (dd,1H), 6.87 (d,2H), 6.82 (d,2H), 6.66 (d,1H), 4.45–4.38 (m,4H), 3.89 (m,2H), 3.68 (m,4H), 3.13 (m,4H), 2.31 (t,2H), 1.73 (m,2H), 1.51 (m2H), 1.26 (s,9H).

(28)

[structure 28: O2S-morpholine-N—C6H4—O—(CH2)10—CO—O—(CH2)2—NH—CO—C6H3(C(CH3)3)—OH]

Yield: 14% of theory ¹H-NMR (250 MHz): 7.69 (d,2H), 7.42 (dd,2H), 6.86 (d,2H), 6.81 (d,2H), 6.73 (d,2H), 6.51 (1,2H,NH), 4.27 (t,2H), 3.88 (t,2H), 3.68 (m,6H), 3.10 (m,4H), 2.31 (t,2H), 1.72 (m,2H), 1.59 (m,2H), 1.38 (s,9H).

EXAMPLES 29–33

The following compounds are prepared by the method described in Example 7, using the corresponding acid chlorides and alcohols as starting materials.

(29)

[structure 29]

Yield: 33% of theory ¹H-NMR (300 MHz): 7.76 (d,1H), 7.49 (dd,1H), 6.67 (d,2H), 6.63 (d,2H), 6.47 (d,1H), 6.42 (bs,1H), 5.27 (m,1H), 4.02 (m,2H), 3.56 (m,2H), 3.47 (m,4H), 3.18 (m,2H), 2.90 (m,4H), 1.26–1.02 (m,18H), 0.62 (t,2×3H).

(30)

[structure 30]

Yield: 30% of theory ¹H-NMR (250 MHz): 7.76 (d,1H), 7.48 (dd,1H), 6.67 (d,2H), 6.63 (d,2H), 6.48 (d,1H), 6.42 (bs,1H,OH), 5.27 (t,1H), 4.03 (d,2H), 3.58 (d,2H), 3.46 (m,4H), 3.19 (m,2H), 2.92 (m,4H),1.26–1.02 (m,18H including t-Bu), 0.62 (t,6H).

(31)

[structure 31]

Yield: 17% of theory ¹H-NMR (250 MHz): 7.77 (d,1H), 7.48 (dd,1H), 6.68 (d,2H), 6.63 (d,2H), 6.48 (d,1H), 5.86 (bs, 1H,OH), 5.16 (t,1H), 3.91 (d,2H), 3.48 (m,4H), 2.91 (m,4H), 1.63–1.02 (m,27H including t-Bu), 0.66 (t,3H).

(32)

[structure 32]

Yield: 53% of theory Elemental analysis: $C_{36}H_{47}NO_7S$ (637.84); calculated: C 64.39% H 7.41% N 2.78%; found: C 63.80% H 7.45% N 2.67%

(33)

[structure 33]

Yield: 54% of theory Melting point: 180°–182° C.

EXAMPLE 34

A solution of 1 part of 4-(1,1-dioxido-thiomorpholin-4-yl)phenol of the formula

[structure]

1, 2 parts of 11-bromoundecanol and 1.3 parts of potassium carbonate in butyl alcohol are refluxed for 4 hours under a nitrogen atmosphere. The product obtained after removal of the solvent is recrystallized from butyl alcohol, to give the compound of the formula (34)

[structure 34: O2S-thiomorpholine-N—C6H4—O—(CH2)11—OH]

having a melting point of 108°–109° C. in a yield of 87% of theory.

EXAMPLE 35

Reaction of 4-(1,1-dioxidothiomorpholin-4-yl)phenol with 6-bromohexanol by the method described in Example 34 gives the compound of the formula (35)

[structure 35: O2S-thiomorpholine-N—C6H4—O—(CH2)6—OH]

having a melting point of 99°–100° C. in a yield of 89% of theory.

EXAMPLE 36

1 part of 4-(1,1-dioxido-thiomorpholin-4-yl)phenol and 1.13 parts of ethylene carbonate are heated at 165° C. for 3.5 hours under nitrogen. After the end of evolution of $CO_2$, the resulting crude product is recrystallized from isopropyl alcohol, to give the compound of the formula (36)

[structure 36: O2S-thiomorpholine-N—C6H4—O—(CH2)2—OH]

having a melting point of 110–111 OC in a yield of 60% of theory.

EXAMPLE 37

1 part of 4-(1,1-dioxido-thiomorpholin-4-yl)phenol and 1.1 parts of methyloxirane

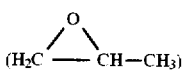

are heated at 100° C. for 4 hours in a closed tube. The crude product is recrystallized from ethanol to give the compound of the formula

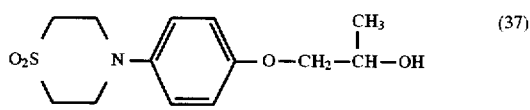

in a yield of 48% of theory. $^1$H-NMR (250 MHz): 6.85 (d.2H), 6.75 (d.2H), 4.15 (m.1H), 3.95 (dd, 1H), 3.75 (dd,1H), 3.65 (m.4H), 3.15 (m.4H), 2.40 (bs,OH), 1.25 (d.3H).

EXAMPLES 38 and 39

A mixture of 1 part of 4-(1,1-dioxido-thiomorpholin-4-yl)phenol, 1.1 parts of n-hexyloxirane and a catalytic amount of ethyltriphenylphosphonium bromide is heated under oxygen at 160° C. until the phenol has disappeared. The crude product is recrystallized from methyl alcohol to give the compound of the formula

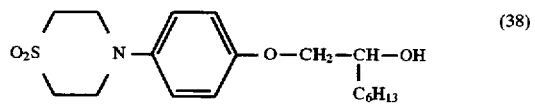

having a melting point of 75°–77° C. in a yield of 54% of theory.

Using decyloxirane, the compound of the formula

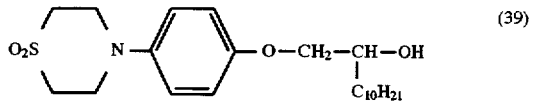

is obtained analogously in a yield of 41% of theory $^1$H-NMR (250 MHz): 6.88 (d.2H), 6.85 (d.2H), 4.15–3.80 (m.3H), 3.67 (m.4H), 3.12 (m.4H), 2.21 (d,1H,OH), 1.55–1.10 (m.18H), 0.86 (t.3H).

EXAMPLE 40

Following the procedure described in Example 38, and using the bisphenol A glycidyl ether of the formula

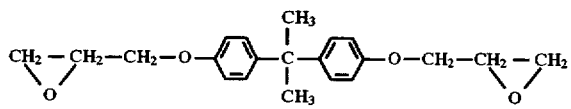

in place of n-hexyloxirane, and adapting the proportional amounts, the compound of the formula

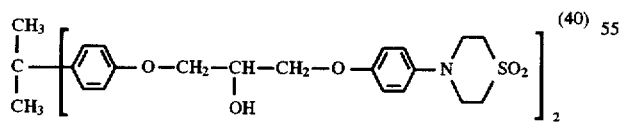

(intermediate for the preparation of compound No. 25) is obtained in a yield of =27% of theory.

$^1$H-NMR (250 MHz): 7.10 (d,4H), 6.87–6.75 (m,12H), 4.35 (m,2H), 4.09 (m,8H), 3.67 (m,4H), 3.11 (m,4H), 2.51 (d, 2H,OH), 1.61 (s, 6H).

EXAMPLES 41 to 43

A solution of 1 part of 4-(11,1-dioxidothiomorpholin-4-yl)phenol, 1.2 parts of Br—(CH$_2$)$_{10}$—CO—O—C$_4$H$_9$ and 1.3 parts of potassium carbonate in butyl alcohol is heated at reflux temperature for 1 1 hours under nitrogen. After evaporation of the solvent, the residue is recrystallized from methyl alcohol to give the compound of the formula

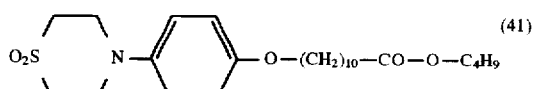

having a melting point of 68° C. in a yield of 45% of theory. Working analogously, the compounds of the formulae

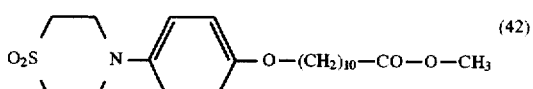

(melting point: 91°–92° C., yield 76% of theory) and

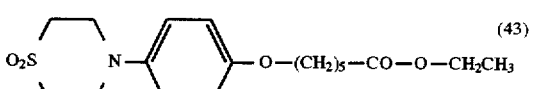

(melting point: 65°–67° C., yield 61% of theory) are obtained.

EXAMPLE 44

Transesterification of the compound 41 with ethylene glycol, using dibutyltin oxide as catalyst and the procedure described in Example 1, gives the compound of the formula

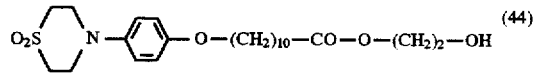

$^1$H-NMR (250 MHz): 6.87 (d,2H), 6.79 (d,2H), 4.18 (m,2H), 3.87 (t,2H), 3.78 (m,2H), 3.67 (m,4H), 3.09 (m,4H), 2.31 (t,2H), 1.75–1.20 (m,16H).

EXAMPLE 45

Reaction of the acid chloride of the formula

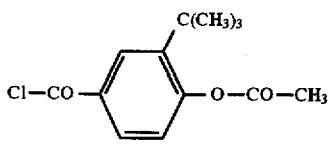

with ethanolamine by the method described in Example 7 gives the compound of the formula

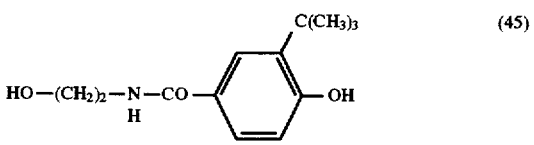

having a melting point of 178°–180° C. in a yield of 67% of theory.

EXAMPLE 46

A polyethylene-coated base material is covered with a gelatine layer containing silver bromide, magenta coupler and a stabilizer.

The gelatine layer includes the following components (per m$^2$ of base material):

| Component | AgBr layer |
|---|---|
| Gelatine | 5.10 g |
| Curing agent | 300 mg |
| Wetting agent | 85 mg |
| Silver bromide | 260 mg |
| Magenta coupler | 305 mg |
| Tricresyl phosphate | 305 mg |
| Stabilizer | *) |

*) The amount of novel stabilizer is 75% by weight, based on the magenta coupler employed. Where a different amount of stabilizer was employed, the corresponding percentage is indicated in the Table in brackets (following the formula number)

The stabilizer is employed either alone or as a mixture with a costabilizer. The curing agent used is 2,4-dichloro-6-hydroxytriazine, and the wetting agent is the sodium salt of diisobutylnaphthalenesulfonic acid.

A step wedge having a density difference of 0.15 logE per step is exposed onto each of the resultant samples, which are subsequently processed in accordance with the manufacturer's instructions by the Kodak EP2 process for colour negative papers.

Following exposure and processing, the remission density in green for the magenta step is measured at a density between 0.9 and 1.1 of the wedge. The wedge is then exposed behind a UV absorber filter in an Atlas exposure unit with 30 kJ/cm², and the remission density is measured again. The drop in magenta dye density (–ΔD) is greatly reduced by the novel stabilizer in comparison with a sample containing no stabilizer.

The values obtained are summarized in Table 1.

TABLE 1

| Magenta coupler of the formula | Novel stabilizer of the formula | Costabilizer of the formula | Percentage colour in density loss (–ΔD) |
|---|---|---|---|
| M-11 | — | — | 93 |
| M-11 | 1 | — | 20 |
| M-11 | 2 | — | 22 |
| M-11 | 3 | — | 20 |
| M-11 | 8 | — | 23 |
| M-11 | 4 | — | 34 |
| M-11 | 5 | — | 19 |
| M-11 | 6 | — | 20 |
| M-11 | 7 | — | 15 |
| M-11 | 9 | — | 23 |
| M-11 | 18 | — | 22 |
| M-11 | 10 | — | 26 |
| M-11 | 11 | — | 24 |
| M-11 | 12 | — | 46 |
| M-11 | 13 | — | 19 |
| M-11 | 14 | — | 23 |
| M-11 | 29 | — | 21 |
| M-11 | 15 | — | 29 |
| M-11 | 16 | — | 32 |
| M-11 | 17 | — | 32 |
| M-11 | 19 | — | 31 |
| M-11 | 20 | — | 26 |
| M-11 | 21 | — | 25 |
| M-11 | 30 | — | 22 |
| M-11 | 31 | — | 24 |
| M-11 | 22 | — | 93 |
| M-11 | 23 | — | 30 |
| M-2 | — | — | 50 |
| M-2 | 8 (50%) | — | 37 |

TABLE 1-continued

| Magenta coupler of the formula | Novel stabilizer of the formula | Costabilizer of the formula | Percentage loss in colour density (–ΔD) |
|---|---|---|---|
| M-2 | 8 (25%) | ST-3 (25%) | 38 |
| M-2 | 7 (50%) | — | 34 |
| M-2 | 7 (25%) | ST-3 (25%) | 33 |
| M-5 | — | — | 84 |
| M-5 | 1 (70%) | — | 20 |
| M-5 | 3 (70%) | — | 18 |
| M-5 | 8 (70%) | — | 20 |
| M-6 | — | — | 38 |
| M-6 | 1 (70%) | — | 6 |
| M-6 | 2 (70%) | — | 6 |
| M-6 | 8 (70%) | — | 8 |

EXAMPLE 47

The following system is cast onto a polyethylene-coated base material:

| |
|---|
| Layer 2 |
| Layer 1 |
| Base |

Layer 1 comprises the following components in the stated amounts (per m²)

| | |
|---|---|
| Gelatine | 5.10 g |
| Curing agent | 300 mg |
| Wetting agent | 85 mg |
| Silver bromide | 260 mg |
| Magenta coupler | as in Table 2 |
| Tricresyl phosphate (TCP) | as in Table 2 |
| Stabilizer(s) | 75% by weight, based on the coupler, unless indicated otherwise in brackets in Table 2 |

Layer 2 comprises the following components in the stated amounts (per m²). Curing and wetting agents are the same as in Example 46.

| | |
|---|---|
| Gelatine | 1.2 g |
| Curing agent | 40 mg |
| Wetting agent | 100 mg |
| Tricresyl phosphate (TCP) | 300 mg |

A step wedge having a density difference of 0.3 logE per step is exposed onto each of the resultant samples, which are subsequently processed in accordance with the Agfa P-94 process for colour negative papers.

Following exposure and processing, the remission density in green for the magenta step is measured at a density between 0.9 and 1.1 of the wedge. The wedge is then exposed behind a UV absorber filter in an Atlas exposure unit with 30 kJ/cm², and the remission density is measured again. The drop in magenta dye density (–ΔD) is greatly reduced by the novel stabilizer in comparison with a sample containing no stabilizer. The values obtained are summarized in Table 2.

TABLE 2

| Magenta coupler of the formula | Amount of coupler | Amount of TCP | Novel stabilizer of the formula | Percentage loss in colour density (−ΔD) |
|---|---|---|---|---|
| M-11 | 305 | 305 | — | 93 |
| M-11 | 305 | 305 | 9 | 29 |
| M-11 | 305 | 305 | 1 | 23 |
| M-11 | 305 | 305 | 3 | 23 |
| M-11 | 305 | 305 | 8 | 25 |
| M-11 | 305 | 305 | 7 | 28 |
| M-11 | 305 | 305 | 13 | 26 |
| M-5 | 253 | 253 | — | 86 |
| M-5 | 253 | 253 | 1 | 25 |
| M-5 | 253 | 253 | 8 | 25 |
| M-6 | 306 | 612 | — | 46 |
| M-6 | 306 | 612 | 8 (35%) | 13 |
| M-6 | 306 | 612 | 7 (35%) | 10 |
| M-6 | 306 | 612 | 1 (35%) | 13 |
| M-2 | 417 | 208 | — | 48 |
| M-2 | 417 | 208 | 1 (50%) | 33 |
| M-2 | 417 | 208 | 7 (50%) | 36 |

EXAMPLE 48

The samples are prepared and processed as described in Example 47. Following exposure and processing, the remission density in green for the magenta step is measured at a density of between 0.9 and 1.1 of the wedge.

The wedges are then irradiated behind a UV absorber filter in the Atlas unit at 100% relative humidity with 30 kJ/cm$^2$, and the remission density is measured again. The results obtained are summarized in Table 3.

TABLE 3

| Magenta coupler of the formula | Amount of coupler | Amount of TCP | Novel stabilizer of the formula | Percentage loss in colour density (−ΔD) |
|---|---|---|---|---|
| M-11 | 305 | 305 | — | 91 |
| M-11 | 305 | 305 | 8 | 61 |
| M-11 | 305 | 305 | 3 | 52 |
| M-11 | 305 | 305 | 7 | 73 |
| M-5 | 253 | 253 | — | 90 |
| M-5 | 253 | 253 | 1 | 42 |
| M-5 | 253 | 253 | 8 | 48 |
| M-5 | 253 | 253 | 7 | 41 |
| M-6 | 306 | 612 | — | 41 |
| M-6 | 306 | 612 | 8 (35%) | 22 |
| M-6 | 306 | 612 | 7 (35%) | 11 |
| M-6 | 306 | 612 | 1 (35%) | 19 |
| M-2 | 417 | 208 | — | 57 |
| M-2 | 417 | 208 | 1 (50%) | 37 |

The amount of stabilizer is 75% by weight, based on the coupler employed, unless stated otherwise. For amounts other than 75% by weight, the corresponding percentage is indicated in brackets.

What is claimed is:

1. A compound of the general formula I

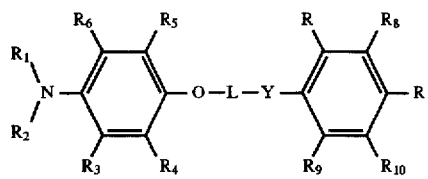

in which one R is the group-OH and the other R is the group R$_7$, and in which:

L is a direct bond or a bridging link of the formulae:

—CO—(C$_1$–C$_{18}$alkylene)$_m$- or
—C$_1$–C$_{18}$alkylene-Q—C$_1$–C$_{18}$alkylene-O—CO—(C$_1$–C$_{18}$alkylene)$_m$-, or a bridging link of the formula —(CH$_2$)$_q$—CH(OR$_{12}$)—R$_{13}$- in which:
Q is a direct bond or is —CH(R$_0$)-,
m is zero or 1, and
q is an integer from 1 to 18;
Y is a divalent bridging link of the formula

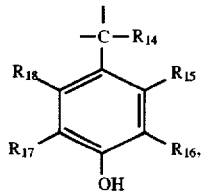

R$_0$ is C$_1$–C$_{18}$alkyl or is C$_2$–C$_{24}$alkyl containing one or more O atoms in the chain, or is a group of the formula

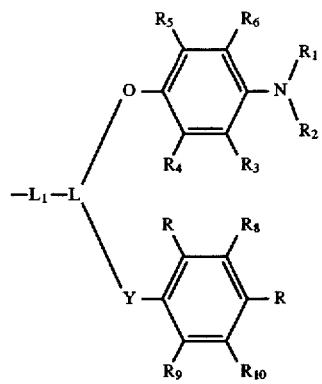

in which L$_1$ is C$_2$–C$_{18}$alkylene or

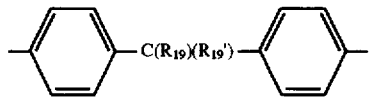

and is connected to the remainder of the molecule by way of a radical L which includes Q(CHR$_0$) or CHR$_0$.

R$_1$ and R$_2$ together form a ring including the divalent group of the formula —(CH$_2$)$_k$—Z—(CH$_2$)$_k$- in which each index k, independently of the other, is an integer from 1 to 3, and Z is the group —O—, —S—, —SO—, —SO$_2$—, —N(R$_{11}$)-, —CH$_2$—, —O—SO—O—, —O—B(R$_{20}$)—, —O—P(R$_{21}$) —O—or —N(R$_{11}$)—(CH$_2$)$_g$—N(R$_{11}$)—, where g is an integer from 1 to 3;

R$_3$ to R$_{10}$ independently of one another are H, C$_1$–C$_{18}$alkyl, C$_1$–C$_{18}$alkenyl, C$_1$–C$_{12}$alkoxy, C$_5$–C$_8$cycloalkyl, unsubstituted or substituted aryl, or halogen, where R$_8$ and R$_{10}$ independently of one another may also be a group of the formula

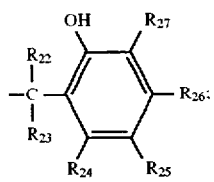

$R_{11}$ and $R_{11}'$ independently of one another are H, $C_1-C_{18}$alkyl, $C_2-C_{18}$alkenyl, unsubstituted or substituted aryl or a group —$COR_{28}$;

$R_{12}$ is H, $C_1-C_{18}$alkyl, $C_2-C_{18}$alkenyl or a group of the formula —$COR_{28}$;

$R_{13}$ is a divalent bridging link of the formula -$(O)_m$-$C_1-C_{18}$alkylene-$(O)_m$-, —O—$C_1-C_{18}$alkylene-O—CO—,   or
—O—$C_1-C_{18}$alkylene-O—CO—$(C_1-C_{18}$alkylene$)_m$-;

$R_{14}$ is H, $C_1-C_{18}$alkyl, $C_2-C_{18}$alkenyl, $C_3-C_8$cycloalkyl, $C_3-C_{24}$alkyl interrupted by one O atoms, unsubstituted or substituted aryl, an unsubstituted or substituted heterocycle, or a group of the formula —$C_1-C_{12}$alkylene-COO—$R_{29}$ or —$C_1-C_{12}$alkylene—CO—$NR_{11}R_{11}'$;

$R_{15}$ to $R_{18}$ independently of one another are H, $C_1-C_{18}$alkyl, $C_2-C_{18}$alkenyl, $C_1-C_{12}$alkoxy, $C_5-C_8$cycloalkyl, unsubstituted or substituted aryl, or halogen;

$R_{19}$ and $R_{19}'$ independently of one another are H, $C_1-C_{18}$alkyl, $C_2-C_{18}$alkenyl or unsubstituted or substituted aryl;

$R_{20}$ and $R_{21}$ are $C_1-C_{18}$alkyl or unsubstituted or substituted aryl;

$R_{22}$ and $R_{23}$ independently of one another are H, $C_1-C_{18}$alkyl, $C_3-C_{24}$alkyl interrupted by one or more O atoms; $C_2-C_{18}$alkenyl; $C_5-C_8$cycloalkyl; unsubstituted or substituted aryl or a group of the formula —$C_1-C_{12}$alkylene-$COOR_{18}$;

$R_{24}$ to $R_{27}$ independently of one another are H, $C_1-C_{18}$alkyl, $C_2-C_{18}$alkenyl, $C_1-C_{12}$alkoxy, $C_5-C_8$cycloalkyl, unsubstituted or substituted aryl, halogen or a group of the formula-$C_1-C_{12}$alkylene-$COOR_{29}$;

$R_{28}$ and $R_{29}$ independently of one another are $C_1-C_{18}$alkyl, $C_2-C_{18}$alkenyl, $C_5-C_8$cycloalkyl or unsubstituted or substituted aryl, and $R_{29}$ is otherwise a group of the formula

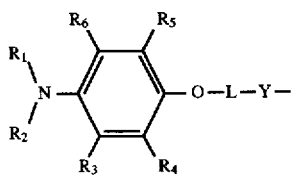

provided that $R_{25}$ is a group of the formula

—$C_1-C_{12}$alkylene-$COOR_{29}$ in which and the other symbols $R_1$, $R_2$, $R_3$, $R_4$, $R_5$, $R_6$ and L are as defined.

2. A compound according to claim 1 in which R ortho to the Y bond is the group $R_7$ and R para to the Y bond is the OH group.

3. A compound according to claim 1 in which Q is a direct bond.

4. A compound according to claim 1 in which $R_1$ and $R_2$ together form a ring including the divalent group of the formula —$(CH_2)_k$—Z—$(CH_2)_k$— in which Z is the group —O—, —S—, —SO—, —SO$_2$—, —N($R_{11}$)—, —OSO—O—, —O—B($R_{20}$)—O—, —O—P($R_{21}$)—O—, —N($R_{11}$)—$(CH_2)_g$—N($R_{11}$)—.

5. A compound according to claim 1 in which Z is —O—, —S—, —SO—, —SO$_2$— or —N($R_{11}$)—.

6. A compound according to claim 5 in which Z is —SO$_2$—.

7. A compound according to claim 1 in which $R_3$ to $R_{10}$ independently of one another are H, $C_1-C_{18}$alkyl, $C_1-C_{12}$alkoxy, $C_5-C_8$cycloalkyl, unsubstituted phenyl or phenyl substituted by $C_1-C_{12}$alkyl or substituted by $C_1-C_{12}$alkoxy.

8. A compound according to claim 7 in which $R_3$, $R_4$, $R_5$, $R_6$, $R_9$ and $R_{10}$ are hydrogen.

9. A compound according to claim 1 in which $R_{11}$ and $R_{11}'$ are H, $C_1-C_{18}$alkyl, unsubstituted phenyl, phenyl substituted by $C_1-C_{12}$alkyl or substituted by $C_1-C_{12}$alkoxy, or $R_{11}$ is the group —$COR_{28}$.

10. A compound according to claim 1 in which $R_{12}$ is H, $C_1-C_{18}$alkyl or —$COR_{28}$.

11. A compound according to claim 1 in which $R_{13}$ is the group

—O—$C_1-C_{18}$alkylene-O—CO—$(C_1-C_{18}$alkylene$)_m$-.

12. A compound according to claim 1 in which $R_{14}$ is H, $C_1-C_{18}$alkyl, $C_3-C_8$cycloalkyl, unsubstituted phenyl, phenyl substituted by $C_1-C_{12}$alkyl or substituted by $C_1-C_{12}$alkoxy, or $R_{14}$ is a 5-membered heterocyclic ring containing a heteroatom.

13. A compound according to claim 1 in which $R_{15}$ to $R_{18}$ independently of one another are H, $C_1-C_{18}$alkyl, $C_1-C_{12}$alkoxy, $C_5-C_8$cycloalkyl, unsubstituted phenyl or phenyl substituted by $C_1-C_{12}$alkyl or substituted by $C_1-C_{12}$alkoxy.

14. A compound according to claim 13 in which $R_8$, $R_9$, $R_{15}$ and $R_{17}$ are hydrogen.

15. A compound according to claim 13 in which $R_{10}$ and $R_{16}$ are $C_1-C_6$alkyl.

16. A compound according to claim 13 in which $R_{18}$ and R ortho to —Y— are hydrogen or a $C_1-C_4$alkyl radical.

17. A compound according to claim 1 in which $R_{19}$ is $C_1-C_{18}$alkyl, unsubstituted phenyl or phenyl substituted by $C_1-C_{12}$alkyl or substituted by $C_1-C_{12}$alkoxy.

18. A compound according to claim 1 in which $R_{20}$ and $R_{21}$ are $C_1-C_{18}$alkyl or unsubstituted phenyl.

19. A compound according to claim 1 in which $R_{22}$ and $R_{23}$ independently of one another are hydrogen, $C_1-C_{18}$alkyl, $C_5-C_8$cycloalkyl, unsubstituted phenyl, phenyl substituted by $C_1-C_{12}$alkyl or substituted by $C_1-C_{12}$alkoxy, or $R_{22}$ and $R_{23}$ are —$C_1-C_6$alkylene-$COOR_{18}$.

20. A compound according to claim 1 in which $R_{24}$ to $R_{27}$ independently of one another are hydrogen, $C_1-C_{18}$alkyl, $C_1-C_{12}$alkoxy, $C_5-C_8$cycloalkyl, unsubstituted phenyl, phenyl substituted by $C_1-C_{12}$alkyl or substituted by $C_1-C_{12}$alkoxy, or $R_{24}$ to $R_{27}$ are the group —$C_1-C_6$alkylene-$COOR_{29}$.

21. A compound according to claim 1 in which $R_{28}$ and $R_{29}$ independently of one another are $C_1-C_{18}$alkyl, $C_5-C_8$cycloalkyl, unsubstituted phenyl, phenyl substituted by $C_1-C_{12}$alkyl or substituted by $C_1-C_{12}$alkoxy, or else $R_{29}$ is the group of the formula
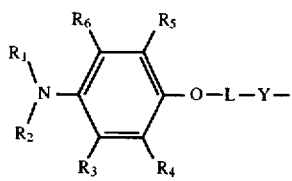
provided that $R_{25}$ is the group —$C_1$–$C_6$alkylene-COOR$_{29}$.
22. A compound according to claim 1 in which $R_{10}$ is H, $C_2$–$C_{18}$alkenyl, $C_1$–$C_{12}$alkoxy, $C_5$–$C_8$cycloalkyl, unsubstituted or substituted aryl, or halogen, where $R_8$ and $R_{10}$ independently of one another are otherwise the group of the formula
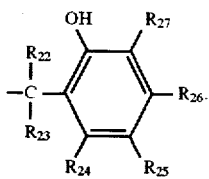
* * * * *